United States Patent [19]
Weiner et al.

[11] Patent Number: 5,830,876
[45] Date of Patent: Nov. 3, 1998

[54] GENETIC IMMUNIZATION

[75] Inventors: David B. Weiner, Merion; William V. Williams; Bin Wang, both of Havertown, all of Pa.

[73] Assignees: The Trustees of the University of Pennsylvania; The Wistar Institute, both of Philadelphia, Pa.

[21] Appl. No.: 453,349

[22] Filed: May 30, 1995

Related U.S. Application Data

[63] Continuation of Ser. No. 29,336, Mar. 11, 1993, abandoned, which is a continuation-in-part of Ser. No. 8,342, Jan. 26, 1993, abandoned.

[51] Int. Cl.$^6$ .......................... A61K 45/05; A61K 48/00; A61K 31/00
[52] U.S. Cl. .......................... 514/44; 424/278.1; 514/615; 514/818
[58] Field of Search ........................ 435/320.1; 424/93.1, 424/93.2, 93.21, 278.1; 514/44, 615, 818

[56] References Cited

U.S. PATENT DOCUMENTS

| | | | |
|---|---|---|---|
| 4,224,404 | 9/1980 | Viza et al. | 435/2 |
| 4,394,448 | 7/1983 | Szoka, Jr. et al. | 435/172.3 |
| 4,806,463 | 2/1989 | Goodchild et al. | 435/5 |
| 4,945,050 | 7/1990 | Sanford et al. | 435/172.1 |
| 5,017,487 | 5/1991 | Stunnenberg et al. | 435/172.3 |
| 5,036,006 | 7/1991 | Sanford et al. | 435/172.3 X |
| 5,466,676 | 11/1995 | Booth et al. | 514/44 |

FOREIGN PATENT DOCUMENTS

WO 93/17706  9/1993  WIPO.

OTHER PUBLICATIONS

Saag et al., Nature Medicine 2(6):625–629 (1996).
A. M. Schultz et al., AIDS 7(suppl. 1):S161–S170 (1993).
V. Glaser, Genetic Engineering News 16(1):6 (1996).
Vandenbark, A., et al., Immunization with a synthetic T–cell receptor v–region peptide protects against experimental autoimmune encephalomyelitis, 1989 *Nature* 341:541–544.
McCoy, M. et al., Human Colon Carcinoma Ki–ras2 Oncogene and Its Corresponding Proto–Oncogene, 1984 *Mol. Cell. Biol.* 4:1577–1582.
Weiner, D.B., et al., Non–CD4 Molecules on Human Cells Important in HIV–1 Cell Entry, (1989) *Vaccines*, Cold Spring Harbor Press, 115–120.
Williams, W.V., et al., Molecular Diagnosis of *Borrelia burgdorferi* Infection (Lyme Disease), 1992 *DNA and Cell. Biol.* 11(3):207–213.
Williams, W.V., et al., Restricted Heterogeneity of T Cell Receptor Transcripts in Rheumatoid Synovium, 1992 *J. Clin. Invest.* 90:326–333.
Wolfe, J.A. et al., Direct Gene Transfer into Mouse Muscle in Vivo, (1990) *Science* 247:1465–1468.
Wolfe, J.A., et al., Conditions Affecting Direct Gene Transfer into Rodent Muscle In Vivo, 1991 *BioTechniques* 11(4):474–485.

Wucherpfennig, K.W., et al., Shares Human T Cell Receptor $V_B$ Usage to Immunodominant Regions of Myelin Basic Protein, 1990 *Science* 248:1016–1019.
Acsadi G., et al., Human dystrophin expression in mdx mice after intramuscular injection of DNA constructs, (1991) *Nature* 352:815–818.
Anilionis, A., et al., Structure of the glycoprotein gene in rabies virus, 1981 *Nature* 294:275–278.
Berman P.W., et al., Protection of chimpanzees from infection by HIV–1 after vaccination with recombinant glycoprotein gp120 but not gp160, (1990) *Nature* 345:622–625.
Chaudhary, V.K., et al., A rapid method of cloning functional variable–region antibody genes in *Escherichia coli* as single–chain immunotoxins, 1990 *Proc. Natl. Acad. Sci. USA* 87:1066–1070.
Chen, Y.H., et al., HIV–1 gp41 contains two sites for interaction with several proteins on the helper T–lymphoid cell line, H9, (1992) *AIDS* 6:533–539.
Cheng–Mayer, C., et al., Human immunodeficiency virus can productively infect cultured human glial cells, (1987) *Proc. Natl. Acad. Sci. USA* 84:3526–3530.
Crowe, J.S., et al., Improved cloning efficiency of polymerase chain reaction (PCR) products after proteinase K digestion, (1991) *Nucl. Acids Res.* 19;184.
Desquenne–Clark, L., et al., T–cell receptor peptide immunization leads to enhanced and chronic experimental allergic encephalomyelitis, 1991 *Proc. Natl. Acad. Sci. USA* 88:7219–7223.
DiFiore, erbB–2 is a Potent Oncogene When Overexpressed in NIH/3T3 Cells, 1987 *Science* 237:178–182.
Anderson, W. French, "Prospects for Human Gene Therapy," *Science* 226:401–409, 1984.
Dubensky et al., "Direct transfection of viral and plasmid DNA into the liver or spleen of mice," *Proc. Natl. Acad. Sci. USA* 81:7529–7533, 1984.
Israel et al., "Biological Activity of Polyoma viral DNA in Mice and Hamsters," *J. of Virology* 29:990–996, 1979.
Langlois et al., "The Ability of Certain SIV Vaccines to Provoke Reactions Against Normal Cells," *Science* 255:292–293, 1992.
Letvin et al., "Risks of Handling HIV," *Nature* 349:573, 1991.

(List continued on next page.)

*Primary Examiner*—George G. Elliott
*Assistant Examiner*—Johnny F. Railey, II
*Attorney, Agent, or Firm*—Woodcock Washburn Kurtz Mackiewicz & Norris LLP

[57] ABSTRACT

A method of immunizing an individual against pathogen is disclosed. Also disclosed is a method of treating an individual who has a hyperproliferative disease, or of treating an individual who is infected by a pathogen. Specifically, the individual is injected with bupivacaine along with DNA in an expressible form, the DNA encoding an antigen. The encoded antigen can be from a protein from the pathogen or from a protein associated with the hyperproliferative disease.

17 Claims, 9 Drawing Sheets

OTHER PUBLICATIONS

Tang et al., "Genetic immunization is a simple method for eliciting an immune response," *Nature* 356:152–154, 1992.

Will et al., "Cloned HBV DNA causes hepatitis in chimpanzees," *Nature* 299:740–742, 1982.

Benoit and Belt, Destruction and regeneration of skeletal muscle after treatment with a local anaesthetic, bupivacaine (Marcaine®) *J. Anat.* 107:547–556, 1970.

Hall–Craggs, E.C.B., Rapid Degeneration and Regeneration of a Whole Skeletal Muscle Following Treatment with Bupivacaine (Marcaine) *Experimental Neurology* 43:349–358, 1974.

Felgner, P.L. and G. Rhodes, Gene therapeutics, (1991) *Nature* 349:351–352.

Fisher, A.G., et al., A molecular clone of HTLV–III with biological activity, (1985) *Nature* 316:262–265.

Fisher, R.A., et al., HIV infection is blocked in vitro by recombinant soluble CD4, (1988) *Nature* 331:76–78.

Goudsmit, J. et al., (1988) *AIDS* 2:157–164.

Hahn and Ebling, Supression of Murine Lupus Nephritis by Administration of an Anti–Idiotypic Antibody to Anti–DNA, 1984 *J. Immunol.* 132(1):187–190.

Howley, P., Papillomavirinae and Their Replication, 1990 *Fields Virology*, vol. 2, Channock, R.M., et al., Eds., Chapter 58:1625–1650.

Howell, M.D., et al., Limited T–cell receptor B–chain heterogeneity among interleukin 2 receptor–positive synovial T cells suggest a role for superantigen in rheumatoid arthritis, 1991 *Proc. Natl. Acad. Sci. USA* 88:10921–10925.

Klein, T.M. et al., Transformation of Microbes, Plants and Animals by Particle Bombardment, (1992) *Bio/technology* 10:286–291.

Koenig, S., et al., Detection of AIDS Virus in Macrophages in Brain Tissues from AIDS Patients with Encephalopathy, (1986) *Science* 233:1089–1093.

Kowalski, M., et al., Functional Regions of the Envelope Glycoprotein of Human Immunodeficiency Virus type 1, (1987) *Science* 237:1351–135.

Lasky, L.A. et al., Neutralization of the AIDS Retrovirus by Antibodies to a Recombinant Envelope Glycoportein, (1986) *Science* 233:209–212.

Lasky, L.A., et al., Delineation of a Region of the Human Immunodeficiency Virus Type 1 gp120 Glycoprotein Critical for Interaction with the CD4 Receptor, (1987) *Cell* 50:975–985.

Maddon, P.J., et al., The T4 Gene Encodes the AIDS Virus Receptor and is Expressed in the Immune System and the Brain, (1986) *Cell* 47:333–348.

Montefiori, D.C., Evaluation of Antiviral Drugs and Neutralizing Antibodies to Human Immunodeficiency Virus by a Rapid and Sensitive Microtiter Infection Assay, (1988) *J. Clin. Microbio.* 26:231–235.

Morgenstern and Land, Advanced mammalian gene transfer: high titre retroviral vectors with multiple drug selection markers and a complementary helper–free packaging cell line, 1990 *Nucl. Acids Res.* 18(12):3587–3596.

Nabel, E.G., et al., Site–Specific Gene Expression in Vivo by Direct Gene Transfer into the Arterial Wall, (1990) *Science* 249:1285–1288.

Nara, P., Quantitative Infectivity Syncytium–Forming Microassay, (1989) *Techniques In HIV Research*, Aldovini & Walker, Eds. 77–86, M Stockton Press.

Oksenberg, J.R., et al., Limited heterogeneity of rearranged T–cell receptor V a transcripts in brains of multiple sclerosis patients, 1990 *Nature* 345:344–346.

Osther, K., et al., Protective Humoral Immune Responses to the Human Immunodeficiency Virus Induced in Immunized Pigs: A Possible Source of Therapeutic Immunoglobulin Preparations, (1991) *Hybridoma* 10:673–683.

Osther, K., et al., The quick Western Blot, A Novel Transportable 50 Minute HIV–1 Antibody Test, (1989) *Transplantation* 47:834–8.

Paliard, X., et al., Evidence for the Effects of a Superantigen in Rheumatoid Arthritis, 1991 *Science* 253:325–329.

Putney, S.D., et al., AIDS The Scientific and Social Challenge, (1989) *Development Of An HIV Subunit Vaccine*, Montreal, V International Conference on AIDS, Abstract Th.C.O. 50.

Schrier, R.D., et al., B–and T–Lymphocyte Responses to an Immunodominant Epitope of Human Immunodeficiency Virus, (1988) *J. Virol.* 62:2531–2536.

Sun, H.C., et al., Generation and Characterization of Monoclonal Antibodies to the Putative CD4–Binding Domain of Human Immunodeficiency Virus Type 1 gp120, 1989 *J. Virol.* 63:3579–85.

Shah and Howley, Papillomaviruses, 1990 *Fields Virology*, Channock, R.M. et al., Eds., vol. 2, Chapter 59, pp. 1651–1676.

Seed, B. and A. Aruffo, Molecular cloning of the CD2 antigen, the T–cell erythrocyte receptor, by a rapid immunoselection procedure, 1987 *Proc. Natl. Acad. Sci. USA* 84:3365–3369.

Szala, S. et al., Molecular cloning of cDNA for the carcinoma–associated antigen GA733–2, 1990 *Proc. Natl. Acad. Sci. USA* 87:3542–3546.

Teitelbaum, D. et al., In Vivo Effects of Antibodies Against A High Frequency Idiotype Of Anti–DNA Antibodies in MRL Mice, 1984 *J. Immunolo.* 132(3):1282–1285.

Thomason, D.B. et al., (1990) American Journal of Physiology 258 (3 Part 1): C578–C582.

Aldovini et al., "Mutations of RNA and Protein Sequences Involved in Human Immunodeficiency Virus Type 1 Packaging Result in Production of Noninfectious Virus," *J. of Virology*, 64:1920–1926, 1990.

Desrosiers, "HIV with Multiple Gene Deletions as a Live Attenuated Vaccine for AIDS," *AIDS Research and Human Retroviruses*, 8:411–421, 1992.

Ronen et al., "Expression of wild–type and mutant p53 proteins by recombinant vaccinia viruses," *Nucleic Acids Research*, 20:3435–3441, 1992.

Benvenisty et al., "Direct introduction of genes into rats and expression of the genes," *Proc. Natl. Acad. Sci. USA*, 83:9551–9555, 1986.

Brandsma et al., "Use of a rapid, efficient inoculation method to induce papillomas by conttontail rabbit papillomavirus DNA shows that the E7 gene is required," *Proc. Natl. Acad. Sci. USA*, 88:4816–4820, 1991.

Friedmann et al., "Progress Toward Human Gene Therapy," *Science*, 244:1275–1281, 1989.

Kaneda et al., "Increased Expression of DNA Cointroduced with Nuclear Protein in Adult Rat Liver," *Science*, 243:375–378, 1989.

Nicolau et al., "In vivo expression of rat insulin after intravenous administration of the liposome–entrapped gene for rat insulin I," *Proc. Natl. Acad. Sci. USA*, 80:1068–1072, 1983.

Seeger et al., "The cloned genome of ground squirrel hepatitis virus is infectious in the animal," *Proc. Natl. Acad. Sci. USA*, 81:5849–5852, 1984.

Wu et al., "Receptor–mediated Gene Delivery and expression in Vivo," *J. of Biological Chemistry*, 263:14621–14624, 1988.

Yang et al., "In vivo and in vitro gene transfer to mammalian somatic cells by particle bombardment," *Proc. Natl. Acad. Sci. USA*, 87:9568–9572, 1990.

Zelenin et al., "High–velocity mechanical DNA transfer of the chloramphenicolacetyl transferase gene into rodent liver, kidney and mammary gland cells in organ explants and in vivo," *FEBS Letts.*, 280:94–96, 1991.

Brigham et al., Rapid Communication: In vivo Transfection of Murine Lungs with a Functioning Prokaryotic Gene Using a Liposome Vehicle; American Journal of the Medical Sciences, Oct. 1989, vol. 298, No. 4, pp. 278–281.

B.D. Davis et al., Eds. *Microbiology*. Third Edition, Hagerstown: Harper and Row, 1980, p. 294.

F.D. Ledley (1991) Human Gene Therapy 2:77–83.

B.F. Haynes (1993) Science 260: 1279–1286.

A. Hoffenbach et al. (1989) The Journal of Immunology 142;452–462.

D. Torpey III et al. (1993) Clinical Immunology and Immunopathology 68(3): 263–272.

L. Butini et al. (1994) Journal of Cell. Biochem. Suppl. 18B:147, Abstr. J306.

A. Knuth et al. (1991) Current Opinion in Immunology 3:659–664.

B. Wang et al. (1993) Proc. Natl. Acad. Sci. USA 90:4156–4160.

D. J. Wells (1993) FEBS Letters 332(1,2):179–182.

GENETIC IMMUNIZATION

CROSS REFERENCE TO RELATED APPLICATIONS

This is a continuation of application Ser. No. 08/029,336, filed Mar. 11, 1993, now abandoned, which is a continuation-in-part of application Ser. No. 08/008,342, filed Jan. 26, 1993, now abandoned.

FIELD OF THE INVENTION

The present invention relates to use of genetic material as immunizing agents. In particular, the present invention relates to the introduction of DNA molecules into an individual's tissues or cells that then can produce proteins capable of eliciting an immune response.

BACKGROUND OF THE INVENTION

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

The immune system can provides multiple means for eliminating targets that are identified as foreign. These means include humoral and cellular responses which participate in antigen recognition and elimination. Briefly, the humoral response involves B cells which produce antibodies that specifically bind to antigens. There are two arms of the cellular immune response. The first involves helper T cells which produce cytokines and elicit participation of additional immune cells in the immune response. The second involves killer T cells, also known as cytotoxic T lymphocytes (CTLs), which are cells capable of recognizing antigens and attacking the antigen including the cell or particle it is attached to.

Vaccination has been singularly responsible for conferring immune protection against several human pathogens. In the search for safe and effective vaccines for immunizing individuals against infective pathogenic agents such as viruses, bacteria, and infective eukaryotic organisms, several strategies have been employed thus far. Each strategy aims to achieve the goal of protecting the individual against pathogen infection by administering to the individual, a target protein associated with the pathogen which can elicit an immune response. Thus, when the individual is challenged by an infective pathogen, the individual's immune system can recognize the protein and mount an effective defense against infection. There are several vaccine strategies for presenting pathogen proteins which include presenting the protein as part of a non-infective or less infective agent or as a discreet protein composition.

One strategy for immunizing against infection uses killed or inactivated vaccines to present pathogen proteins to an individual's immune system. In such vaccines, the pathogen is either killed or otherwise inactivated using means such as, for example, heat or chemicals. The administration of killed or inactivated pathogen into an individual presents the pathogen to the individual's immune system in a noninfective form and the individual can thereby mount an immune response against it. Killed or inactivated pathogen vaccines provide protection by directly generating T-helper and humoral immune responses against the pathogenic immunogens. Because the pathogen is killed or otherwise inactivated, there is little threat of infection.

Another method of vaccinating against pathogens is to provide an attenuated vaccine. Attenuated vaccines are essentially live vaccines which exhibit a reduced infectivity. Attenuated vaccines are often produced by passaging several generations of the pathogen through a permissive host until the progeny agents are no longer virulent. By using an attenuated vaccine, an agent that displays limited infectivity may be employed to elicit an immune response against the pathogen. By maintaining a certain level of infectivity, the attenuated vaccine produces a low level infection and elicits a stronger immune response than killed or inactivated vaccines. For example, live attenuated vaccines, such as the poliovirus and smallpox vaccines, stimulate protective T-helper, T-cytotoxic, and humoral immunities during their nonpathogenic infection of the host.

Another means of immunizing against pathogens is provided by recombinant vaccines. There are two types of recombinant vaccines: one is a pathogen in which specific genes are deleted in order to render the resulting agent non-virulent. Essentially, this type of recombinant vaccine is attenuated by design and requires the administration of an active, non-virulent infective agent which, upon establishing itself in a host, produces or causes to be produced antigens used to elicit the immune response. The second type of recombinant vaccine employs non-virulent vectors which carry genetic material that encode target antigens. This type of recombinant vaccine similarly requires the administration of an active infective non-virulent agent which, upon establishing itself in a host, produces or causes to be produced, the antigen used to elicit the immune response. Such vaccines essentially employ non-virulent agents to present pathogen antigens that can then serve as targets for an anti-pathogen immune response. For example, the development of vaccinia as an expression system for vaccination has theoretically simplified the safety and development of infectious vaccination strategies with broader T-cell immune responses.

Another method of immunizing against infection uses subunit vaccines. Subunit vaccines generally consist of one or more isolated proteins derived from the pathogen. These proteins act as target antigens against which an immune response may be mounted by an individual. The proteins selected for subunit vaccine are displayed by the pathogen so that upon infection of an individual by the pathogen, the individuals immune system recognizes the pathogen and mounts a defense against it. Because subunit vaccines are not whole infective agents, they are incapable of becoming infective. Thus, they present no risk of undesirable virulent infectivity that is associated with other types of vaccines. It has been reported that recombinant subunit vaccines such as the hepatitis B surface antigen vaccine (HBsAg) stimulate a more specific protective T-helper and humoral immune response against a single antigen. However, the use of this technology to stimulate board protection against diverse pathogens remains to be confirmed.

Each of these types of vaccines carry severe drawbacks which render them less than optimally desirable for immunizing individuals against a particular pathogen.

It has been observed that absent an active infection, a complete immune response is not elicited. Killed and inactivated vaccines, because they do not reproduce or otherwise undergo an infective cycle, do not elicit the CTL arm of the cellular immune response in most cases. Additionally, killed and inactivated vaccines are sometimes altered by the means used to render them inactivated. These changes can sometimes affect the immunogenicity of the antigens. Subunit vaccines, which are merely discreet components of a pathogen, do not undergo any sort of infective cycle and often do not elicit the CTL arm of the cellular immune response. Absent the CTL arm, the immune response elicited by either vaccine is often insufficient to adequately protect an individual. In addition, subunit vaccines have the additional drawback of being both expensive to produce and purify.

Attenuated vaccines, on the other hand, often make very effective vaccines because they are capable of a limited, non-virulent infection and result in immune responses involving a humoral response and both arms of the cellular immune response. However, there are several problems associated with attenuated vaccines. First, it is difficult to test attenuated vaccines to determine when they are no longer pathogenic. The risk of the vaccine being virulent is often too great to properly test for effective attenuation. For example, it is not practically possible to test an attenuated form of Human Immunodeficiency virus (HIV) to determine if it is sufficiently attenuated to be a safe vaccine. Secondly, attenuated vaccines carry the risk of reverting into a virulent form of the pathogen. There is a risk of infecting individuals with a virulent form of the pathogen when using an attenuated vaccine.

Recombinant vaccines require the introduction of an active infective agent which, in many cases, is undesirable. Furthermore, in cases where the recombinant vaccine is the result of deletion of genes essential for virulence, such genes must exist and be identified. In vaccines in which pathogen genes are inserted into non-virulent vectors, many problems exist related to the immune response elicited against the vector antigens which negatively impact the immune response elicited against the target antigen. First, the recombinant vaccine introduces a great number of vector antigens against which the immune system also responds. Secondly, the vector can be used only once per individual since, after the first exposure, the individual will develop immunity to the vector. These problems are both present, for example, in recombinant vaccines that employ vaccinia vectors such as those disclosed in U.S. Pat. No. 5,017,487 issued May 21, 1991 to Stunnenberg et al. This technology has not been universally successful against diverse pathogenic organisms and it is also complicated by the large amount of excess vaccinia antigens presented in the vaccinee. Once vaccinated with the vaccinia vector, the vaccinee cannot be effectively vaccinated again using the vaccinia vector.

Accordingly, the most effective vaccines for invoking a strong and complete immune response carry the most risk of harming the individual while the safer alternatives induce an incomplete, and are therefore, less effective immune response. Furthermore, many subunit vaccines and recombinant vaccines using non-virulent vectors to produce target proteins are most useful if a single antigenic component can be identified which is singularly protective against live challenge by a pathogen. However, both technologies require that the protective component be identified. Such identification is often both laborious and time-consuming.

A distinct advantage would exist if there were a rapid system for directly testing subunit vaccination strategies without tissue culture and in the absence of excess vector antigens. Furthermore, it would be particularly advantageous if such a system could deliver an antigen that could be presented for development of both T cell immune arms.

There is a need for a means to immunize individuals against pathogen infection which can elicit a broad, biologically active protective immune response without risk of infecting the individual.

PCT International Application Number PCT/US90/01515 published Oct. 4, 1990 discloses methods of immunizing an individual against pathogen infection by directly injecting polynucleotides into the individual's cells in a single step procedure. The stimulation of inoculated cells is neither disclosed nor suggested. An HIV vaccine is disclosed which consists of the introduction of polynucleotides that encode the viral protein gp120. The operability of this vaccine is not evidenced.

HIV infection represents a great threat to the human population today. Despite the intense resources expended and efforts made to develop an effective vaccine, the problem remains intractable. No vaccine is currently available that protects an individual against HIV infection. There is a great need for a method of immunizing an individual against HIV infection. There is a great need for an effective immunotherapy method to combat the development of AIDS in HIV infecting individuals.

In addition to immunizing against pathogens, work has recently been undertaken to develop vaccines against cancer. Cancer vaccines currently being studied are essentially analogous to anti-pathogen subunit vaccines. Anti-cancer subunit vaccines essentially introduces a cancer-associated target protein into an individual. An immune response is elicited against the target protein in the same manner an immune response is elicited against a pathogen protein in the individual. The target protein is a protein that is specific to cancer cells. Subsequent appearance of that protein when cancer occurs provides an immunogenic target for an immune response. Thus, the cancer vaccine immunizes an individual against cancer cells, an "endogenous pathogen", by setting out a target antigen specifically associated with the cancer. Specific proteins are administered which represent targets for an immunological response. As in the case of anti-pathogen subunit vaccines, the immune response elicited is often incomplete and insufficient to protect the individual. In particular, administration of a protein or peptide does not elicit a CTL response.

There is a need for an effective means to immunize individuals against hyperproliferative disease such as cancer in order to provide individuals with broad, biologically active protective immunity against specifically targeted hyperproliferating cells.

Many autoimmune diseases are mediated by specific antigen receptors. Autoimmune diseases generally refer to those diseases involving a self-directed immune response. Autoimmune diseases are referred to as being B cell mediated or T cell mediated. For example, Systemic Lupus Erythematosus (SLE) is considered a B cell mediated autoimmune disease. Many of the clinical manifestations of SLE are believed to be due to the presence of anti-DNA antibodies in the patients' serum, which combine with the antigen to form immune complexes. These immune complexes are deposited in tissues, setting off the inflammatory cascade. Rheumatoid Arthritis (RA) is an example of T cell mediated autoimmune disease. RA is believed to be mediated by autoreactive T cells present in the synovium (joint tissue), where they respond to an unknown antigen in the context of class II major histocompatibility complex (MHC II) molecules, such as HLA-DR4 which is genetically linked to RA. These T cells recognize a specific antigen associated with MHC II via their T cell antigen receptors (TCRs). Thus, autoreactive antigen receptors, such as antibodies or T cell antigen receptors are responsible for the initial recognition event in a series of pathogenic, inflammatory events which culminates in the clinical manifestations of autoimmune diseases such as SLE and RA.

Several studies have been performed in experimental systems where such autoreactive antigen receptors have been targeted or deleted. Animal model systems for autoimmune disease include a murine lupus model which occurs in a strain of NZB/NZW mice, and an experimental allergic encephalomyelitis (EAE) model which can be produced in susceptible mouse and rat strains following inoculation with myelin basic protein (MBP). In murine SLE, anti-idiotypic antibodies have been used therapeutically in an attempt to delete the autoreactive B cells which produce the autoreactive antibodies. In some cases, these anti-idiotypic antibodies have improved clinical manifestations of the disease (Hahn, B. H. and F. M. Ebling, 1984 J. Immunol. 132(1):187–190), while in others they have worsened disease (Teitelbaum, D. et al., 1984 J. Immunol. 132(3):1282–1285). Similarly, in EAE, antibodies to autoreactive T cell antigen receptors have been utilized, as has been immunization with T cell antigen receptor-derived peptides. Again, in some instances this improves the disease Vandenbark, A., et al., 1989 Nature 341:541–544, while in other worsening of the disease occurs (Desquenne-Clark, L., et al., 1990 Proc. Natl. Acad. Sci. USA 88:7219–7223).

Thus, while it is possible to vaccinate against autoimmune disease in some cases, the nature of the immune response elicited affects the clinical outcome of such therapies. For example, if the vaccination results in development of an antibody response, with subsequent anti-idiotype development, these anti-idiotypic antibodies could target the autoreactive B cells or T cells for complement-mediated lysis, with resulting clinical improvement. Alternatively, if the immunization results in production of non-complement fixing anti-idiotypic antibodies, these would bind to the autoreactive B cells or T cells and cross-link their antigen receptors. Typically, this leads to activation of the cells and subsequent increased production of the autoreactive antibodies or T cells, with worsening of the clinical condition. Alternatively, if a predominant T cell response is elicited by vaccination, this could result in either a helper T cell response which would be expected to worsen disease or a killer/suppressor cell response which should improve the disease.

There is a need for an effective means to immunize individuals against and treat individuals suffering from autoimmune diseases which would elicit a CTL response capable of targeting either B cells that produce the antibodies involved in the disease (in the case of B cell mediated autoimmune disease) or the T cells that produce the specific T cell antigen receptor which are involved in the disease (in the case of T cell mediated autoimmune disease).

The direct introduction of a normal, functional gene into a living animal has been studied as a means for replacing defective genetic information. In such studies, DNA is introduced directly into cells of a living animal.

Nabel, E. G., et al., (1990) Science 249:1285–1288, disclose site-specific gene expression in vivo of a beta-galactosidase gene that was transferred directly into the arterial wall in mice.

Wolfe, J. A. et al., (1990) Science 247:1465–1468, disclose expression of various reporter genes that were directly transferred into mouse muscle in vivo. The use of direct gene transfer as an alternative anti-pathogen vaccination method is suggested.

Acsadi G., et al., (1991) Nature 352:815–818, disclose expression of human dystrophin gene in mice after intramuscular injection of DNA constructs.

Wolfe, J. A., et al., 1991 BioTechniques 11(4):474–485, which is incorporated herein by reference, refers to conditions affecting direct gene transfer into rodent muscle in vivo. Multiple injections of plasmid DNA are reported to result in higher levels of protein production but not to the extent that the levels of protein production are proportional to additional plasmid DNA added.

Felgner, P. L. and G. Rhodes, (1991) Nature 349:351–352, disclose direct delivery of purified genes in vivo as drugs without the use of retroviruses. Use of direct gene transfer by single injection are suggested as a possible vaccination strategy and a cellular immune response to HIV gp120 resulting from introduction of plasmid DNA encoding the same into cells is reported to have been observed.

SUMMARY OF THE INVENTION

The present invention relates to a method of immunizing an individual against a pathogen. The method comprises the steps of contacting cells of said individual with a cell stimulating agent and administering to the cells, a DNA molecule that comprises a DNA sequence that encodes a pathogen antigen operatively linked to regulatory sequences. The DNA molecule is capable of being expressed in the cells of the individual.

The present invention relates to a method of immunizing a human against HIV. The method comprises the steps of administering two different DNA molecules to different cells of the human. Each DNA molecule comprises a DNA sequence that encodes HIV antigen operatively linked to regulatory sequences. Each DNA molecule is capable of being expressed in human cells. The different DNA molecules encode different HIV structural proteins which are selected from the group consisting of gag, pol and env.

The present invention is related to a method of immunizing an individual against a hyperproliferative disease. The method comprises the steps of administering to cells of an individual, a DNA molecule that comprises a DNA sequence that encodes a hyperproliferative disease-associated protein operatively linked to regulatory sequences; the DNA molecule being capable of being express in the cells.

The present invention relates to a method of immunizing an individual against an autoimmune disease. The method comprises the steps of administering to cells of an individual, a DNA molecule that comprises a DNA sequence that encodes an autoimmune disease-associated protein operatively linked to regulatory sequences; the DNA molecule being capable of being expressed in the cells.

The present invention relates to an HIV vaccine comprising two inoculants. The first inoculant comprises a pharmaceutically acceptable carrier or diluent and a first DNA molecule. The first DNA molecule comprises a DNA sequence that encodes at least one HIV structural protein operatively linked to regulatory sequences; the DNA molecule being capable of being expressed in human cells. The second inoculant comprises a pharmaceutically acceptable carrier or diluent and a second DNA molecule. The second DNA molecule comprises a DNA sequence that encodes at least one HIV structural protein operatively linked to regulatory sequences; the DNA molecule being capable of being expressed in human cells. The first and second DNA molecules are different and, taken together, encode HIV structural proteins gag, pol and env.

DETAILED DESCRIPTION OF THE INVENTION

Figure 1A:
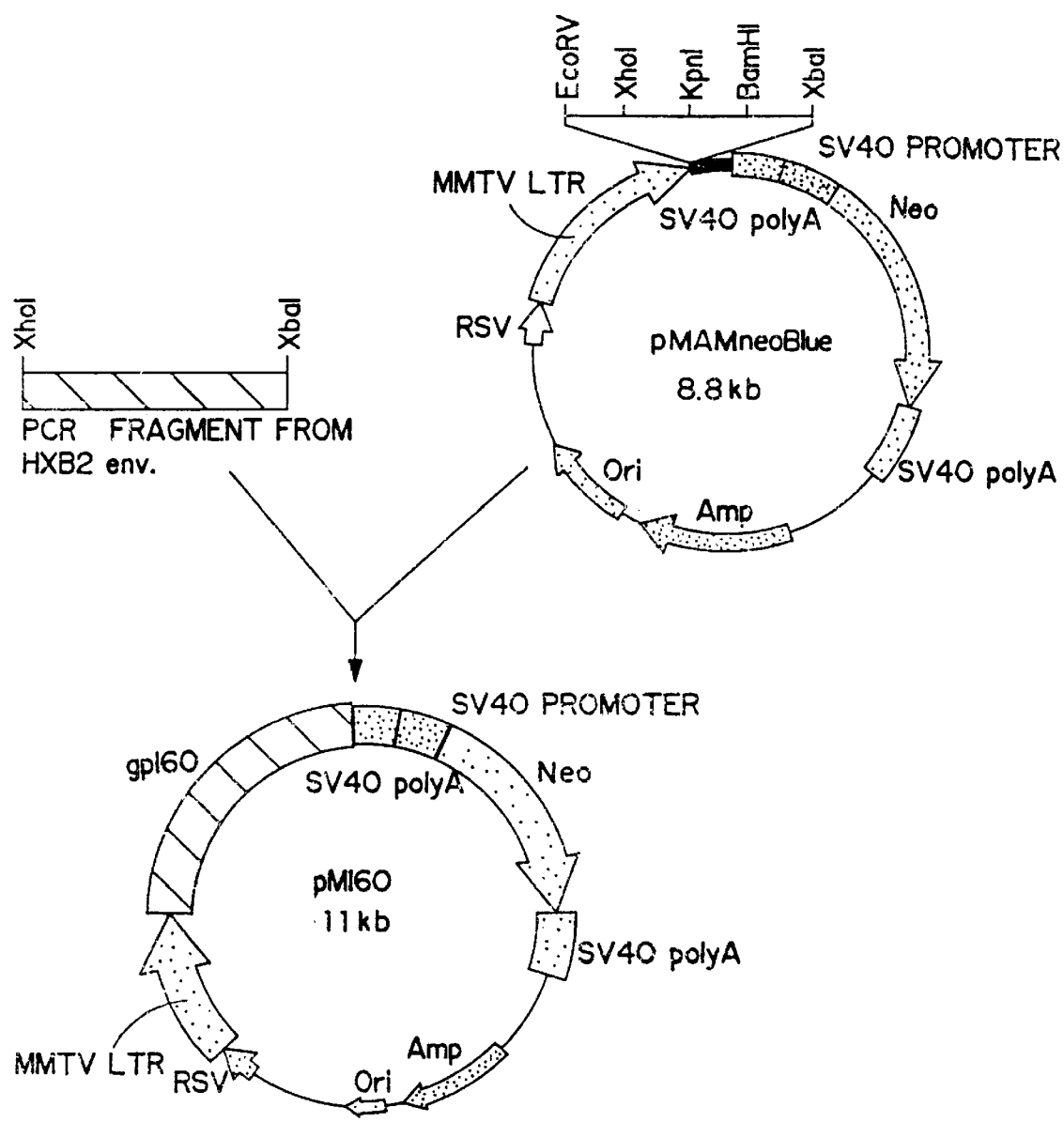
FIG. 1A is a diagram depicting the construction of plasmid pM160 which was produced by inserting a PCR-generated fragment that encodes the HIV-HXB2 glycoprotein gp160 into plasmid pMAMneoBlue (Clonetech).

The present invention relates to methods of eliciting immune responses in an individual which can protect an individual from pathogen infection or combat diseases and disorders involving cells that produce specific proteins. According to the present invention, genetic material that encodes an immunogenic protein is directly administered to an individual's cells either in vivo or ex vivo. The genetic material is expressed by the individual's cells to form immunogenic target proteins that elicit an immune response. The resulting immune response is broad based: in addition to a humoral immune response, both arms of the cellular immune response are elicited. Thus, the immune responses elicited by vaccination methods of the present invention are particularly effective to protect against pathogen infection or combat cells associated with hyperproliferative diseases or autoimmune diseases.

The present invention is useful to elicit broad immune responses against a target protein. Target proteins may be proteins specifically associated with pathogens or the individual's own "abnormal" cells. The present invention is useful to immunize individuals against pathogenic agents and organisms such that an immune response against a pathogen protein provides protective immunity against the pathogen. The present invention is particularly useful to protect an individual against infection by non-encapsulated intracellular pathogens which produce proteins within the host cells. The immune response generated against such proteins is capable of eliminating infected cells with CTLs. The present invention is useful to combat hyperproliferative diseases and disorders such as cancer by eliciting an immune response against a target protein that is specifically associated with the hyperproliferative cells. In such cases, a cytotoxic immune response against the hyperproliferating cells which produce the target protein is elicited. The present invention is useful to combat autoimmune diseases and disorders by eliciting an immune response against a target protein that is specifically associated with cells involved in the autoimmune condition. In such cases, the cytotoxic immune response against cells that produce the target protein is provided.

The immune response elicited by the target protein that is produced by vaccinated cells in an individual is a broad-based immune response which includes B cell and T cell responses including cytotoxic T cell (CTL) responses. It has been observed that target antigen produced within the cells of the host are processed intracellularly: broken down into small peptides, bound by Class I MHC molecules, and expressed on the cell surface. The Class I MHC-target antigen complexes are capable of stimulating CD8$^+$ T-cells, which are phenotypically the killer/suppressor cells. Genetic immunization according to the present invention is thus capable of eliciting cytotoxic T-cell (CTL) responses (killer cell responses). It has been observed that genetic immunization according to the present invention is more likely to elicit CTL responses than other methods of immunization.

The CTL response is crucial in protection against pathogens such as viruses and other intracellular pathogens which produce proteins within infected cells. Similarly, the CTL response can be utilized for the specific elimination of deleterious cell types which, during their production of proteins, display antigens bound by Class I MHC molecules. Therefore, genetic immunization according to the present invention is more likely to result in anti-pathogen protection, anti-cancer activity and clinical improvement in patients suffering autoimmune diseases than standard immunization using killed, inactivated or protein- or peptide-based subunit vaccines.

Genetic immunization according to the present invention elicits an effective immune response without the use of infective agents or vectors. Vaccination techniques which usually do produce a CTL response do so through the use of an infective agent. A complete, broad based immune response is not generally exhibited in individuals immunized with killed, inactivated or subunit vaccines. The present invention achieves the full complement of immune responses in a safe manner without the risks and problems associated with vaccinations that use infectious agents.

According to the present invention, cells are treated with compounds that stimulate cell division in order to facilitate uptake of genetic constructs. This step provides an improved method of direct uptake of genetic material. Administration of cell stimulating compounds results in a more effective immune response against the target protein encoded by the genetic construct.

According to the present invention, DNA or RNA that encodes a target protein is introduced into the cells of an individual where it is expressed, thus producing the target protein. The DNA or RNA is linked to regulatory elements necessary for expression in the cells of the individual. Regulatory elements include a promoter and a polyadenylation signal. In addition, other elements may also be included in the genetic construct.

As used herein, the term "genetic construct" refers to the DNA or RNA molecule that comprises a nucleotide sequence which encodes the target protein and which includes initiation and termination signals operably linked to regulatory elements including a promoter and polyadenylation signal capable of directing expression in the cells of the vaccinated individual. As used herein, the term "expressible form" refers to gene constructs which contain the necessary regulatory elements operable linked to a coding sequence of a target protein, such that when present in the cell of the individual, the coding sequence will be expressed. As used herein, the term "genetic vaccine" refers to a pharmaceutical preparation that comprises a genetic construct.

The present invention provides genetic vaccines which comprise genetic constructs that contain DNA or RNA that encodes a target protein. As used herein, the term "target protein" refer to a protein against which an immune response can be elicited. The target protein is an immunogenic protein derived from the pathogen or undesirable cell-type such as a cancer cell or a cell involved in autoimmune disease. Target proteins are, depending upon the type of genetic vaccine, either pathogen-associated proteins, proteins associated with hyperproliferating cells, or proteins associated with auto-immune disorders. The immune response directed against the target protein will protect the individual against the specific infection or disease with which the target protein is associated. For example, a genetic vaccine with a DNA or RNA molecule that encodes a pathogen-associated target protein is used to elicit an immune response that will protect the individual from infection by the pathogen. Likewise, a genetic vaccine with a DNA or RNA molecule that encodes a target protein associated with a hyperproliferative disease such as, for example, a tumor-associated protein, is used to elicit an immune response directed at hyperproliferating cells. A genetic vaccine with a DNA or RNA molecule that encodes a target protein that is associated with T cell receptors or antibodies involved in autoimmune diseases is used to elicit an immune response that will combat the autoimmune disease by eliminating cells in which the natural form of target protein is being produced.

The genetic construct of genetic vaccines comprise a nucleotide sequence that encodes a target protein operably linked to regulatory elements needed for gene expression. Accordingly, incorporation of the DNA or RNA molecule into a living cell results in the expression of the DNA or RNA encoding the target protein and thus, production of the target protein.

When taken up by a cell, the genetic construct which includes the nucleotide sequence encoding the target protein operably linked to the regulatory elements may remain present in the cell as a functioning episomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Since integration into the chromosomal DNA necessarily requires manipulation of the chromosome, it is preferred to maintain the DNA construct as an episome. This reduces the risk of damaging the cell by splicing into the chromosome without affecting the effectiveness of the vaccine. Alternatively, RNA may be administered to the cell.

The necessary elements of a genetic construct of a genetic vaccine include a nucleotide sequence that encodes a target protein and the regulatory elements necessary for expression of that sequence in the cells of the vaccinated individual. The regulatory elements are operably linked to the DNA sequence that encodes the target protein to enable expression. The nucleotide sequence that encodes the target protein may be cDNA, genomic DNA, synthesized DNA or a hybrid thereof or an RNA molecule such as mRNA. Accordingly, as used herein, the terms "DNA construct", "genetic construct" and "nucleotide sequence" are meant to refer to both DNA and RNA.

The regulatory elements necessary for gene expression include: a promoter, an initiation codon, a stop codon, and a polyadenylation signal. It is necessary that these elements be operable in the vaccinated individual. Moreover, it is necessary that these elements be operably linked to the nucleotide sequence that encodes the target protein such that the nucleotide sequence can be expressed in the cells of a vaccinated individual and thus the target protein can be produced.

Initiation codons and stop codon are generally considered to be part of a nucleotide sequence that encodes the target protein. However, it is necessary that these elements are functional in the vaccinated individual.

Similarly, promoters and polyadenylation signals used must be functional within the cells of the vaccinated individual.

Examples of promoters useful to practice the present invention, especially in the production of a genetic vaccine for humans, include but are not limited to Mouse Mammary Tumor Virus (MMTV) promoter, Human Immunodeficiency Virus Long Terminal Repeat (HIV LTR) promoter, Moloney virus, ALV, Cytomegalovirus (CMV) promoter, human Actin, human Myosin, RSV, human Hemoglobin, human muscle creatine and EBV.

Examples of polyadenylation signals useful to practice the present invention, especially in the production of a genetic vaccine for humans, include but are not limited to SV40 polyadenylation signal and LTR polyadenylation signals.

In addition to the regulatory elements required for DNA expression, other elements may also be included in the DNA molecule. Such additional elements include enhancers. The enhancer may be selected from the group including but not limited to: human Actin, human Myosin, CMV, RSV, human Hemoglobin, human muscle creatine and EBV.

Genetic constructs can be provided with mammalian origin or replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. When the construct is introduced into the cell, tk will be produced. The drug gangcyclovir can be administered to the individual and that drug will cause the selctive killing of any cell producing tk. Thus, a system can be provided which allows for the selective destruction of vaccinated cells.

In order to be a functional genetic construct, the regulatory elements must be operably linked to the nucleotide sequence that encodes the target protein. Accordingly, it is necessary for the promoter and polyadenylation signal to be in frame with the coding sequence. In order to maximize protein production, regulatory sequences may be selected which are well suited for gene expression in the vaccinated cells. Moreover, codons may be selected which are most efficiently transcribed in the vaccinated cell. One having ordinary skill in the art can produce DNA constructs which are functional in vaccinated cells.

In order to test expression, genetic constructs can be tested for expression levels in vitro using tissue culture of cells of the same type as those to be vaccinated. For example, if the genetic vaccine is to be administered into human muscle cells, muscle cells grown in culture such as solid muscle tumors cells of rhabdomyosarcoma may be used as an in vitro model to measure expression level.

One aspect of the present invention provides a method of conferring a broad based protective immune response against pathogen infection without the use of infectious agents. It has been discovered that introducing a genetic construct that includes a nucleotide sequence which encodes immunogenic pathogen-derived proteins into cells administered a compound which stimulates cell division results in the production of those proteins in the vaccinated cells of an individual. These proteins are processed within the cell and become bound to Class I MHC molecules. The protein-MHC I bound complexes elicit a broad biologically active immune response in the individual that includes CTLs. The CTLs attack infected cells and can therefore protect against infection by the pathogen without the use of an infective vector.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins.

Table 1 provides a listing of some of the viral families and genera for which vaccines according to the present invention can be made. DNA constructs that comprise DNA sequences which encode the listed target antigens are useful in vaccines.

In addition to being particularly effective against pathogens which infect the cells of an individual, the present invention is also useful to immunize an individual against other pathogens including prokaryotic and eukaryotic protozoan pathogens as well as multicellular parasites. Table 2 contains a list of bacterial and eukaryotic pathogens for which vaccines according to the present invention may be made.

In order to produce a genetic vaccine to protect against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens.

The genetic construct used in the genetic vaccine can include genetic material which encodes many pathogen antigens. For example, several viral genes may be included in a single construct thereby providing multiple targets. In addition, multiple inoculants which can be delivered to different cells in an individual can be prepared to include a complete or near complete set of genes in the vaccine. This allows for the introduction of more than a single antigen target and eliminates the requirement that protective antigens be identified.

The ease of handling and inexpensive nature of DNA and RNA further allow for more efficient means of screening for protective antigens. Genes can be sorted and systematically tested much more easily than proteins. The pathogenic agents and organism for which the vaccine is being produced to protect against is selected and an immunogenic protein is identified. Tables 1 and 2 include lists of some of the pathogenic agents and organisms for which genetic vaccines can be prepared to protect an individual from infection by them.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. These proteins can elicit a broad biologically active immune response in the individual including CTLs that can effectively combat and eliminate hyperproliferating cells in the individual. Thus, to immunize against hyperproliferative diseases, a genetic construct that includes a nucleotide sequence which encodes a protein that is associated with a hyperproliferative disease is administered to an individual. When expressed, the protein produced elicits an immune response directed at cells that produce the protein.

In order for the hyperproliferative-associated protein to be an effective immunogenic target, it must be a protein that is produced exclusively or at higher levels in hyperproliferative cells as compared to normal cells.

Such target proteins include those which are proteins encoded by oncogenes. Generally, oncogenes can be divided into three groups depending upon the portion of the cell where their gene products are found. Oncogenes such as myb, myc, fyn, and the translocation gene bcl/abl encode products that remain in the nucleus and are involved in transcription and cell cycle events. Gene products of oncogenes such as ras, sarc and P53 are generally found in the cytoplasm. Membrane bound products of oncogenes include neu, trk and EGRF. While protein products of these genes are often found in normal cells, they exist at greater levels in cancer cells. Thus, cancer cells can be expected to be more likely to have these proteins bound to Class I MHC molecules at the cell surface. Accordingly, CTLs which specifically recognize the target protein/MHC I complex will be more effective against cancer cells.

In addition to oncogene products as target antigens, variable regions of antibodies made by B cell lymphomas and variable regions of T cell receptors of T cell lymphomas can also be used as target antigens. These antigens are discussed and described in greater detail below in the section referring to autoimmune disease. However, it is contemplated that similar vaccination strategies can be used for treating and preventing these types of cancer.

Additionally, other tumor-associated proteins can be used as target proteins. Such proteins are generally those which are found at higher levels in tumor cells. Examples include protein 17-1A and fully binding proteins.

While the present invention may be used to immunize an individual against one or more of several forms of cancer, the present invention is particularly useful to immunize an individual who is predisposed to develop a particular cancer or who has had cancer and is therefore susceptible to a relapse.

Developments in genetics and technology as well as epidemiology allow for the determination of probability and risk assessment for the development of cancer in individual. Using genetic screening and/or family health histories, it is possible to predict the probability a particular individual has for developing any one of several types of cancer. Those individuals identified as being predisposed to developing a particular form of cancer can, by using the methods of the present invention, take prophylactic steps towards reducing the risk of cancer. According to the present invention, high-risk individuals can be immunized against the form of cancer that they have a predisposition to develop.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and "self"-directed antibodies.

T cell mediated autoimmune diseases include Rheumatoid arthritis (RA), multiple sclerosis (MS), Sjogrens, sarcoidosis, insulin dependent diabetes mellitus (IDDM), autoimmune thyroiditis, reactive arthritis, ankylosing sponduilitis, scleroderma, paymyositis, dermatomyositis, psorisis, vasculitis, Wegner's granulomatosis, Crohn's disease and colitis. Each of these diseases is characterized by high affinity T cell receptors that bind to endogenous antigens and initiate the inflammatory cascade associated with autoimmune diseases. Vaccination against the variable region of the high affinity T cells would elicit an immune response including CTLs to eliminate those T cells.

In RA, several specific variable regions of T cell receptors (TCRs) which are involved in the disease have been characterized. These TCRs include V$\beta$-3, V$\beta$-14, V$\beta$-17 and V$\alpha$-28. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921–10925; Paliard, X., et al., 1991 *Science* 253:325–329; Williams, W. V., et al., 1992 *J. Clin. Invest.* 90:326–333; each of which is incorporated herein by reference.

In MS, several specific variable regions of TCRs which are involved in the disease have been characterized. These TCRs include V$\beta$-7 and V$\alpha$-10. Thus, vaccination with a DNA construct that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include V$\beta$-6, V$\beta$-8, V$\beta$-17 and V$\alpha$-16. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myathon, myasthinia gravas, autoimmune hemolytic anemia, autoimmune thrombocytopenia, asthma, cryobulinemia, primary biliary sclerosis and pernias anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, the antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

According to the invention, the genetic vaccine may be administered directly into the individual to be immunized or ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the genetic vaccine may be introduced by various means into cells that are removed from the individual. Such means include, for example, transfection, electroporation and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines according to the present invention comprise about 0.1 to about 1000 micrograms of DNA. In some preferred embodiments, the vaccines contain about 1 to about 500 micrograms of DNA. In some preferred embodiments, the vaccines contain about 25 to about 250 micrograms of DNA. Most preferably, the vaccines contain about 100 micrograms DNA.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline are preferred. Stabilizers include gelatin and albumin.

According to the present invention, prior to or contemporaneously with administration of the genetic construct, cells may be administered a "cell stimulating" or "cell proliferative" agent. As used herein, the terms "cell stimulating agent" or "cell proliferative agent" are used interchangeably and refer to compounds which stimulate cell division. Such compounds facilitate DNA and RNA uptake.

In a preferred embodiment, bupivacaine, a well known and commercially available pharmaceutical compound, is administered prior to or contemporaneously with the genetic construct. Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, *The Pharmacological Basis of Therapeutics*, Eds.: Gilman, A. G. et al, 8th Edition, Chapter 15:3111, which is incorporated herein by reference. Compounds that display a functional similarity to bupivacaine may be useful in the method of the present invention.

In addition to bupivacaine, mepivacaine, lidocaine and other similarly acting compounds, other contemplated cell stimulating agents include lectins, growth factors, cytokines and lymphokines such as platelet derived growth factor (PDGF), gCSF, gMCSF, epidermal growth factor (EGF) and IL-4.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). About 50 $\mu$l to about 2 ml of 0.5% bupivacaine-HCl and 0.1% methylparaben in an isotonic pharmaceutical carrier may be administered to the site where the vaccine is to be administered, preferably, 50 $\mu$l to about 1500 $\mu$l, more preferably about 1 ml.

The genetic construct may be combined with collagen as an emulsion and delivered intraperatonally. The collagen emulsion provides a means for sustained release of DNA. 50 $\mu$l to 2 ml of collagen are used. About 100 $\mu$g DNA are combined with 1 ml of collagen in a preferred embodiment using this formulation.

In some embodiments of the invention, the individual is first subject to bupivacaine injection prior to genetic vaccination by intramuscular injection. That is, up to, for example, about 24 hrs prior to vaccination, the individual is first injected with bupivacaine. Alternatively, bupivacaine can be injected simultaneously, minute before or after vaccination.

In some embodiments of the invention, the individual is subject to a series of vaccinations to produce a full, broad immune response. According to this method, at least two and preferably four injections are given over a period of time. The period of time between injections may include from 24 hours apart to two weeks or longer between injections, preferably one week apart. Alternatively, at least two and up to four separate injections are given simultaneously at different parts of the body.

In some embodiments of the invention, a complete vaccination includes injection of two or more different inoculants into different tissues. For example, in an HIV vaccine according to the invention, the vaccine comprises two inoculants in which each one comprises genetic material encoding different viral proteins. This method of vaccination allows the introduction of a up to a complete set of viral genes into the individual without the risk of assembling an infectious viral particle. Thus, an immune response against most or all of the virus can be invoked in the vaccinated individual. Injection of each inoculant is performed at different sites, preferably art a distance to ensure no cells receive both genetic constructs. As a further safety precaution, some genes may be deleted or altered to further prevent the capability of infectious viral assembly.

While the disclosure herein primarily relates to uses of the methods of the present invention to immunize humans, the methods of the present invention can be applied to veterinary medical uses too. It is within the scope of the present invention to provide methods of immunizing non-human as well as human individuals against pathogens and protein specific disorders and diseases. Accordingly, the present invention relates to genetic immunization of mammals, birds and fish. The methods of the present invention can be particularly useful for mammalian species including human, bovine, ovine, porcine, equine, canine and feline species.

While this disclosure generally discusses immunization in the context of prophylactic methods of protection, the term "immunizing" is meant to refer to both prophylactic and therapeutic methods. Thus, a method of immunizing includes both methods of protecting an individual from pathogen challenge or occurrence or proliferation of specific cells as well as methods of treating an individual suffering from pathogen infection, hyperproliferative diseaze or autoimmune disease. Accordingly, the present invention may be used as a vaccine for prophylactic protection or in a therapeutic manner; that is, as immunotherapeutic methods and preparations.

The Examples set out below include representative examples of aspects of the present invention. The Examples are not meant to limit the scope of the invention but rather serve exemplery purposes. In addtion, various aspects of the invention can be summarized by the following description. However, this description is not meant to limit the scope of the invention but rather to highlight various aspects of the invention. One having ordinary skill in the art can readily appreciate additional aspects and embodiments of the invention.

The present invention relates to a method of immunizing an individual against a pathogen comprising the steps of contacting cells of the individual with a cell stimulating agent and administering to cells of the individual, a DNA molecule that comprises a DNA sequence that encodes a pathogen antigen operatively linked to regulatory sequences; the DNA sequence is capable of being expressed in the cells. In some preferred embodiments, the individual is a human. In some preferred embodiments, the cell stimulating agent is bupivacaine. In some preferred embodiments, the DNA molecule is administered to cells in vivo. In some preferred embodiments, the DNA molecule is administered intramuscularly. In some preferred embodiments, the pathogen is an intracellular pathogen. In some preferred embodiments, the pathogen is a virus. In some preferred embodiments, the pathogen is a virus selected from the group consisting of: human immunodeficiency virus, HIV; human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus. In some preferred embodiments, the pathogen is human immunodeficiency virus. In some preferred embodiments, the pathogen is HIV and said DNA molecule comprises a DNA sequences that encodes an HIV structural protein. In some preferred embodiments, the DNA molecule comprises a promoter selected from the group consisting of: Mouse Mammary Tumor Virus (MMTV) promoter, Human Immunodeficiency Virus Long Terminal Repeat (HIV LTR) promoter, Moloney, ALV, Cytomegalovirus (CMV) promoter human Actin, human Myosin, RSV, human Hemoglobin, human muscle creatine and EBV. In some preferred embodiments, the DNA molecule further comprises an enhancer. In some preferred embodiments, the DNA molecule further comprises an enhancer selected from the group consisting of: human Actin, human Myosin, CMV, RSV, human Hemoglobin, human muscle creatine and EBV. In some preferred embodiments, at least two or more different DNA molecules are administered to different cells of an individual; the different DNA molecules each comprise DNA sequences encoding one or more pathogen antigens of the same pathogen. In some preferred embodiments: the individual is a human; the cell stimulating agent is bupivacaine; the pathogen is human immunodeficiency virus; at least two or more different DNA molecules are administered to different cells of an individual; and the different DNA molecules each comprise DNA sequences encoding one or more human immunodeficiency virus antigens. In some preferred embodiments: the individual is a human; the cell stimulating agent is bupivacaine; the pathogen is human immunodeficiency virus; two different DNA molecules are administered to different cells of an individual; and the different DNA molecules encode different HIV structural proteins. In some preferred embodiments: the individual is a human; the cell stimulating agent is bupivacaine; the pathogen is human immunodeficiency virus; two different DNA molecules are administered to different cells of an individual; one of the DNA molecules comprises a DNA sequences that encodes HIV structural proteins gag and pol; and the other of the DNA molecules comprises a DNA sequences that encodes HIV structural proteins env. In some preferred embodiments: the individual is a human; the cell stimulating agent is bupivacaine; the pathogen is human immunodeficiency virus; two different DNA molecules are administered to different cells of an individual; one of the DNA molecules comprises a DNA sequences that encodes HIV structural proteins gag; and the other of the DNA molecules comprises a DNA sequences that encodes HIV structural proteins pol and env.

The present invention relates to a method of immunizing a human against HIV comprising the steps of: administering to cells of the human, two different DNA molecules; each of the DNA molecules comprising a DNA sequence that encodes at least one HIV antigen operatively linked to regulatory sequences; the DNA sequences being capable of being expressed in the cells; DNA sequences of each of the different DNA molecules encode different HIV structural proteins; the DNA sequences encoding structural proteins encode at least one of the HIV proteins encoded by HIV genes selected from the group consisting of gag, pol and env.

The present invention relates to a method of immunizing an individual against a hyperproliferative disease comprising the steps of: administering to cells of the individual, a DNA molecule comprising DNA sequence that encodes a hyperproliferative disease-associated protein operatively linked to regulatory sequences; the DNA sequence is capable of being expressed in the cells. In some preferred embodiments, the individual is a human. In some preferred embodiments, the cell stimulating agent is bupivacaine. In some preferred embodiments, the DNA molecule is administered to cells in vivo. In some preferred embodiments, the DNA molecule is administered intramuscularly. In some preferred embodiments, the hyperproliferative disease is cancer. In some preferred embodiments, the DNA molecule comprises a DNA sequence encoding a target protein selected from the group consisting of: protein products of oncogenes myb, myc, fyn, ras, sarc, neu and trk; protein products of translocation gene bcl/abl; P53; EGRF; variable regions of antibodies made by B cell lymphomas; and variable regions of T cell receptors of T cell lymphomas. In some preferred embodiments, the DNA molecule comprises a promoter selected from the group consisting of: Mouse Mammary Tumor Virus (MMTV) promoter, Human Immunodeficiency Virus Long Terminal Repeat (HIV LTR) promoter, Moloney, ALV, Cytomegalovirus (CMV) promoter human Actin, human Myosin, RSV, human Hemoglobin, human muscle creatine and EBV. In some preferred embodiments, the DNA molecule further comprises an enhancer. In some preferred embodiments, the DNA molecule further comprises an enhancer selected from the group consisting of: human Actin, human Myosin, CMV, RSV, human Hemoglobin, human muscle creatine and EBV.

The present invention relates to a method of immunizing an individual against an autoimmune disease comprising the steps of: administering to cells of said individual, a DNA molecule comprising DNA sequence that encodes an autoimmune disease-associated protein operatively linked to regulatory sequences; the DNA sequence is capable of being expressed in said cells. In some preferred embodiments, the individual is a human. In some preferred embodiments, the cell stimulating agent is bupivacaine. In some preferred embodiments, the DNA molecule is administered to cells in vivo. In some preferred embodiments, the DNA molecule is administered intramuscularly. In some preferred embodiments, the DNA molecule comprises a DNA sequence encoding a target protein selected from the group consisting of: variable regions of antibodies involved in B cell mediated autoimmune disease; and variable regions of T cell receptors involved in T cell mediated autoimmune disease. In some preferred embodiments, the DNA molecule comprises a promoter selected from the group consisting of: Mouse Mammary Tumor Virus (MMTV) promoter, Human Immunodeficiency Virus Long Terminal Repeat (HIV LTR) promoter, Moloney, ALV, Cytomegalovirus (CMV) promoter human Actin, human Myosin, RSV, human Hemoglobin, human muscle creatine and EBV. In some preferred embodiments, the DNA molecule further comprises an enhancer. In some preferred embodiments, the DNA molecule further comprises an enhancer selected from the group consisting of: human Actin, human Myosin, CMV, RSV, human Hemoglobin, human muscle creatine and EBV.

The present invention relates to an HIV vaccine comprising at least two inoculants. A first inoculant comprises a pharmaceutically acceptable carrier or diluent and a first DNA molecule that comprises a DNA sequence that encodes at least one HIV structural protein operatively linked to regulatory sequences; the DNA sequence is capable of being expressed in human cells. A second inoculant comprises a pharmaceutically acceptable carrier or diluent and a second DNA molecule that comprises a DNA sequence that encodes at least one HIV structural protein operatively linked to regulatory sequences; the said DNA sequence is capable of being expressed in human cells. The first DNA molecule is not identical to the second DNA molecule and, taken together, the first DNA molecule and the second DNA molecule encode HIV structural proteins gag, pol and env. In some preferred embodiments, the HIV vaccine further comprises a third inoculant comprising bupivacaine.

EXAMPLES

Example 1

According to the present invention, an effective vaccine has been produced which can invoke a protective immune response against HIV infected cells as well as cell free virus. As the awareness of AIDS and HIV infection has grown, repeated attempts and vast expenditures of resources and efforts have been made to produce an HIV vaccine. Despite enormous efforts, little progress has been made thus far and the long felt need for an HIV vaccine has gone unabated.

The present invention provides an HIV vaccine using direct genetic immunization. Genetic constructs are provided which, when delivered into the cells of an individual, are expressed to produce HIV proteins. The production of all viral structural proteins in the cells of the individual elicit a protective immune response which protects against HIV infection. The HIV vaccine of the present invention may be used to immunize uninfected individuals from HIV infection or serve as an immunotherapeutic for those individuals already infected. The HIV vaccine of the present invention invokes an immune response including CTLs which recognize and attack HIV infected cells and recognize the widest contingent of HIV protein. Thus, uninfected individuals are protected from HIV infection.

In a preferred embodiment, the present invention relates to a method of immunizing an individual against HIV. According to this embodiment, the immunization comprises administration of two inoculants. These two inoculants comprise at least two and preferably more than two, a plurality or all of the genes of the HIV virus. However, the inoculants are not delivered together. Accordingly, an inoculated cell will not be administered a complete complement of genes. The vaccinated individual will receive at least two different and preferably more than two, more preferably a plurality or all of the viral genes. Immune responses can then be directed at the total complement of HIV protein target.

This strategy serves two purposes. First, it is unknown which target protein is most effective as an immunizing antigen to protect an individual against infection. Thus, immunizing with two or more provides a greater probability that the vaccinated individual will be provided with sufficient immunogenic target proteins for eliciting a protective immune response. Secondly, HIV proteins are known to undergo structural changes due to mutation. By providing multiple antigenic targets, the probability that a viral particle will escape detection by the immune response is reduced despite structural changes in one or more viral proteins. Accordingly, it is desirable to vaccinate an individual with multiple and preferably a nearly complete or complete complement of genes encoding viral proteins.

If a single cell is provided with a complete complement of viral genes, it is possible that a complete infectious virus can be assembled within the cell. Accordingly, a genetic construct according to the present invention is not provided with such a full complement of genes. Furthermore, two or more inoculants, each having an incomplete set of genes and combined having up to a full complement of viral genes, are administered to different cells, preferably at a distant site from each other to ensure that no vaccinated cell will inadvertently be exposed to a full set of genes. For example, a portion of the HIV genome may be inserted into a first construct and the remaining portion of the HIV genome is inserted in a second construct. The first construct is administered to an individual as a genetic vaccine in the muscle tissue of one arm while the second construct is administered to an individual as a genetic vaccine in the muscle tissue of the individual's other arm. The individual may be exposed to a full set of viral genes; thus essentially vaccinating against the whole virus but with no risk that an infectious viral particle will be assembled.

As an additional safety precaution, even when genetic material is delivered by two or more inoculants at distant parts of the individual's body, one or more essential genes can be deleted or intentionally altered to further ensure that an infectious viral particle cannot be formed. In such embodiments, the individual is not administered a complete functional set of viral genes.

A further safety precaution provides non-overlapping portions of the viral genome on the separate genetic constructs that make up the separate inoculants respectively. Accordingly, recombination between the two genetic constructs is prevented.

In a preferred embodiment of the present invention, a full complement of structural genes are provided. The structural genes of HIV consist of gag, pol and env. These three genes are provided on two different DNA or RNA constructs. Accordingly, in one preferred embodiment, gag and pol are on one DNA or RNA construct and env is on another. In another preferred embodiment, gag is on one DNA or RNA construct and pol and env is on the other. In another preferred embodiment, gag and env are on one DNA or RNA construct and pol is on the other. Optionally, in any of these combinations, HIV regulatory genes may also be present. The HIV regulatory genes are: vpr, vif, vpu, nef, tat and rev.

The DNA construct in a preferred embodiment consists of a promoter, an enhancer and a polyadenylation signal. The promoter may be selected from the group consisting of: HIV LTR, human Actin, human Myosin, CMV, RSV, Moloney, MMTV, human Hemoglobin, human muscle creatine and EBV. The enhancer may be selected from the group consisting of: human Actin, human Myosin, CMV, RSV, human Hemoglobin, human muscle creatine and EBV. The polyadenylation signal may be selected from the group consisting of: LTR polyadenylation signal and SV40 polyadenylation signal among others.

In a preferred embodiment, the two inoculant vaccine is administered intramuscularly at spatially segregated tissue of the individual, preferably in different appendages, such as for example in the right and left arms. Each inoculant of the present invention may contain from about 0.1 to about 1000 micrograms of DNA. Preferably, each inoculant contains about 1 to about 500 micrograms of DNA. More preferably, each inoculant contains about 25 to about 250 micrograms of DNA. Most preferably, each inoculant contains about 100 micrograms DNA.

The inoculant in a preferred embodiment is in a sterile isotonic carrier, preferably phosphate buffered saline or saline solution.

In a preferred embodiment, prior to vaccine administration, the tissue to be vaccinated is injected with a cell proliferating agent, preferably bupivacaine. Bupivacaine injections may be performed up to about 24 hours prior to vaccination. It is contemplated that bupivacaine injection will occur immediately before vaccination. About 50 $\mu$l to about 2 ml of 0.5% bupivacaine-HCl and 0.1% methylparaben in isotonic NaCl is administered to the site where the vaccine is to be administered, preferably, 50 $\mu$l to about 1500 $\mu$l, more preferably about 1 ml.

Accordingly, a preferred embodiment comprises a two inoculant vaccine: one inoculant comprising a DNA or RNA construct having two HIV structural genes, the other inoculant comprising a DNA or RNA construct having the third, remaining HIV structural gene such that the combined inoculants contain a full complement of HIV structural genes. The structural genes on each DNA or RNA construct are operable linked to a promoter, an enhancer and a polyadenylation signal. The same or different regulatory elements may control expression of the viral genes. When vaccinating an individual, the two inoculants are administered intramuscularly to different sites, preferably on different arms. In a preferred embodiment of the invention, bupivacaine is first administered at the site where inoculant is to be administered.

In a preferred embodiment, the vaccination procedure is repeated at least once and preferably two or three times. Each vaccination procedure is performed from 24 hours to two months apart.

Preferred genetic constructs include the following.

Plasmids and Cloning Strategies:

Two plasmids were constructed: one which contains HIV gap/pol and the other which contains HIV env.

The HIV-1 genomic clone pNL43 was obtained through the NIH AIDS Research and Reference Reagent Program (ARRRP), Division of AIDS, NIAID, NIH, from Dr. Malcom Martin, and can be used as the starting material for HIV-1 viral genes for genetic constructs. Alternatively, any HIV molecular clone of infected cell can, through use of the polymerase chain technology, be modified sufficiently for construction including the HXB2 clone the MN clone as well as the SF or BAL-1 clone. The pNL43 clone is a construct that consists of HIV-1 proviral DNA plus 3 kb of host sequence from the site of integration cloned into pUC18.

Construction of pNL-puro-env plasmid:

This plasmid was constructed for expression of gag pol. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

Cloning strategy for deletion of vpr regulatory gene from the HIV gag pol vector:

A region from just upstream of the unique PflMI site to just after the vif termination codon was amplified via PCR using primers that introduced a non-conservative amino acid change (glu→val) at amino acid 22 of vpr, a stop codon in the vpr reading frame immediately after amino acid 22, and an EcoRI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus.

Plasmid construction for envelope expression:

The DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AGGCGTCTCGAGACAGAGGAGAGCAAGAAATG-3' (SEQ ID NO:1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. Gene specific amplification was performed using Taq DNA polymerase according to the manufacturer's instructions (Perkin-Elmer Cetus Corp.). The PCR reaction products were treated with 0.5 ug/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAM-neoBlue (Clontech Laboratories, Inc., Palo Alto, Calif.). The resulting construct was designated as pM160. The plasmid DNA was purified with CsCl gradient ultracentrifugation.

An alternative envelope expression plasmid construction called HIV-1 env-rev plasmid:

The region encoding the two exons of rev and the vpu and envelope open reading frames of HIV-1 HXB2 was amplified via PCR and cloned into the expression vector pCNDA/neo (Invitrogen). This plasmid drives envelope production through the CMV promoter.

Example 2

In experiments designed to compare the immunogenic response elicited by genetic vaccination and protein vaccination, animal models were designed using tumor cells that specifically express a foreign target protein. Three immune competent mouse models have been developed which express foreign antigens. Three clonal tumor cell lines which are derived from the Balb/c mouse strain are used. The cell lines are: 1) a lymphoid cell line which does not metastasize significantly to other tissues but forms large palpable tumors which appear to kill the animal within an 8–12 week period; 2) a murine melanoma cell line with some ability to metastize, mostly to the lung, and in which, following inoculation with 1 million cells, results in the development in the mice of large palpable tumors which similarly kill the animal within 10–12 weeks; and 3) a murine lung adenocarcinoma cell line which metastasizes to multiple tissues and kills the animal within 12 or more weeks. Subclones have been selected which can display foreign antigens in an unrecognized form. When transfected tumors are implanted into a parent mouse strain, unlike the majority of similar murine tumor lines, the animals do not make a protective immune response to the foreign antigens displayed and the tumors are accepted. These tumors then kill the animal with the same phenotype in the same time frame as the original untransfected tumor. Using these models, the immune response elicited by genetic vaccination against an antigen can be measured.

It was observed that mice vaccinated with a genetic vaccine comprising a genetic construct that resulted in production of the target protein by the cells of the mouse elicited an immune response including a strong cytotoxic response that completely eliminated tumors displaying the target protein but with no effect on tumors that did not. In mice inoculated with the target protein itself, the immune response elicited thereby was much less effective. The tumors were reduced in size but, due to an absence of a cytotoxic response, they were not eliminated. As controls, untransfected tumors were used in experiments comparing the immune response of animals vaccinated with the genetic vaccine, subunit vaccine and unvaccinated animals. These experiments clearly demonstrate that the genetic vaccine produced a broader, more effective immune response which was capable, by virtue of CTL's, of completely eliminating tumors. By contrast, immunization using intact target protein produced a more limited, less effective immune response.

Example 3

In some embodiments of the invention, the infectious virus, HIV, which is responsible for AIDS is the pathogenic agent against which a genetic vaccine has been designed. The viral protein gp160, which is processed into gp120 and gp41, is the target protein against which a genetic vaccine is produced. The genetic vaccine contains a DNA construct that comprises a DNA sequence encoding gp160 operably linked regulatory elements. When administered to an individual, the DNA construct of the genetic vaccine is incorporated into the cells of the individual and gp160 is produced. The immune response that is elicited by the protein is broad based and includes the humoral and both arms of the cellular immune response. The broad biological response provides superior protection to that achieved when the protein itself is administered.

The following is a description of the use of genetic immunization for elicitation of an anti-human immunodeficiency virus type 1 (HIV-1) immune response in mice by administering a DNA construct that contains a DNA sequence which encodes the HIV envelope glycoprotein gp160. The gp160 construct (pM160) expresses biologically active HIV-1 envelope proteins in vivo.

Mice were injected intramuscularly with pM160and subsequently analyzed for anti-HIV immune responses. The antisera from animals immunized in this manner produce anti-HIV envelope glycoprotein immune responses as measured by enzyme linked immunosorbent assay (ELISA) and immunoprecipitation assays. The antisera neutralizes HIV-1 infection and inhibits HIV-1 induced syncytium formation.

The observed neutralization and anti-syncytial activity may be the result of reactivity of the elicited antibodies to functionally important regions of the HIV-1 envelope protein, such as the V3 loop of gp120, CD4 binding site and the N-terminal "immunodominant" region of gp41, among others.

The DNA construct (pM160) encoding the HIV-1/HXB2 (Fisher, A. G., et al., (1985) *Nature* 316:262–265) gp160 membrane bound glycoprotein under control of a RSV enhancer element with the MMTV LTR as a promoter (FIG. 1A) was tested to determine whether this membrane-bound protein, when expressed by endogenous cells, can generate an anti-pathogen immune responses. The construct was generated as follows. The DNA segment encoding the envelope gene of HIV-1 HXB2 was cloned by the polymerase chain reaction (PCR) technique amplification utilizing the lambda cloned DNA obtained from eh AIDS repository. The sequences of the 5' and 3' primers are 5'-AGGCGTCTCGAGACAGAGGAGAGCAAGAAATG-3' (SEQ ID NO:11) with incorporation of XhoI site and 5'-TTTCCCTCTAGATAAGCCATCCAATCACAC-3' (SEQ ID NO:12) with incorporation of XbaI site, respectively, which encompass gp160, tat and rev coding region. Gene specific amplification was performed using Taq DNA polymerase according to manufacturer's instruction (Perkin-Elmer Cetus Corp.) The PCR reaction products were treated with 0.5 µg/ml proteinase K at 37° C. for thirty minutes followed by a phenol/chloroform extraction and ethanol precipitation (Crowe, J. S., et al., (1991) *Nucl. Acids Res.* 19:184). Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech, Inc.). The resulting construct was designated as pM160. The plasmid DNA was purified with CsCl purification (Sambrook, J. et al., (1989 *Molecular Cloning: A Laboratory Manual*, Cold Spring Harbor Laboratory Press, Cold Spring Harbor, N.Y.).

The pM160 construct, which contains a DNA sequence that encodes gp160, was transfected into a human rhabdomyosarcoma cell line, TE671 (Stratton, M. R., et al., (1989) *Carcinogenesis* 10:899–905), to evaluate its expression before introduction into living animals. Transfection of pM160 construct into TE671 cells was performed according to Wang, B., et al., (1992) *AIDS Human Retr.*, in press. Briefly, 2 μg of purified pM160 was added to 2×10⁶ TE671 cells (Stratton, M. R., et al., (1989) *Carcinogenesis* 10:899–905) and subject to electroporation. Following electroporation, the cells were grown in fresh medium for forty eight hours prior to the addition of 500 μg/ml neomycin for selection. Individual cells expressing gp160 envelope protein were isolated by binding to M450 magnetic beads (Dynal) which was coated with mixture of monoclonal anti-gp120 antibodies, namely ID6, AD3 and AC4 (Ugen, K. E. et al., (1992) *Generation of Monoclonal Antibodies Against the Amino Region of gp120 Which Elicits Antibody Dependent Cellular Cytotoxicity*, Cold Spring Harbor Laboratory, 1992). Clones were isolated by limiting dilution of the gp160 expressing cells. One of such clone was designated as the 3G7 cell line. Expression of gp120 and gp41 was determined by Western blot analysis of whole cell lysates of 3G7 cells versus vector-alone transfected TE671 cells, performed as previously described (Osther, K., et al., (1989) *Transplantation* 47:834–8; and Weiner, D. B., et al., (1989) *Vaccines*, Cold Spring Harbor Press, 115–120).

Figure 1B:
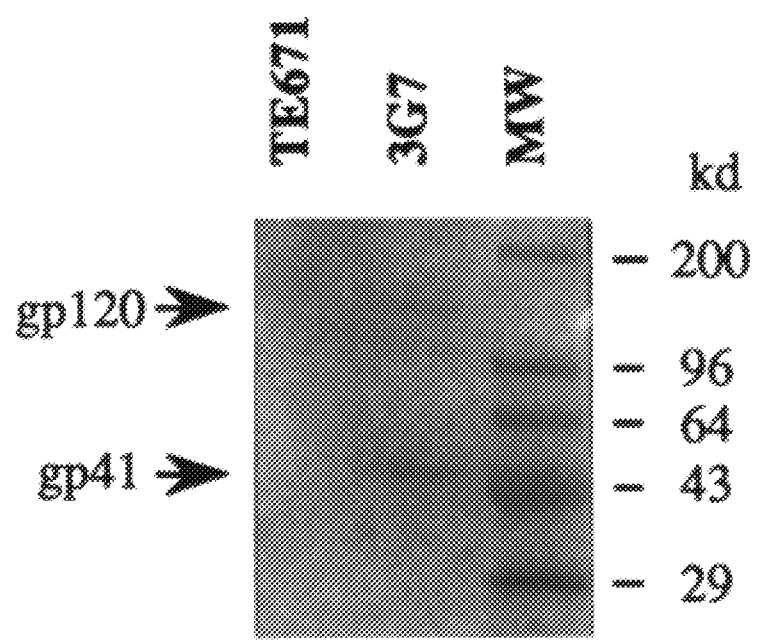
FIG. 1B is a photograph of an autoradiogram of a Western blot of whole cell lysates of cells transfected with the pM160 plasmid (3G7 cells) versus vector-alone transfected cells (TE671 cells) showing production of gp120 and gp41 in 3G7 cells and not in TE671 cells.

Typically, the mature HIV envelope glycoprotein gp160 is processed into gp120 and gp41 (Kowalski, M., et al., (1987) *Science* 237:1351–135). The expression of HIV gp120 and gp41 by the pM160 transfected cell line 3G7 were observed in Western blot analysis with anti-gp160 specific serum (Osther, K., et al., (1991) *Hybridoma* 10:673–683) (FIG. 1B). Functional expression of gp160 by this cell line was further demonstrated by the ability of 3G7 but not TE671 cells to fuse with several CD4⁺ T-cell cell lines.

In the genetic immunization procedure described herein, the quadriceps muscles of BALB/c mice were injected with 100 μl of 0.5% bupivacaine-HCl and 0.1% methylparaben in isotonic NaCl using a 27-gauge needle to stimulate muscle cell regeneration (Thomason, D.B. et al., (1990) *Cell Physiol.* 27:C578–581). Twenty-four hours later, the same injection sites were then injected with either 100 μg of pM160 or with 100 μg of pMAMneoBlue as a control plasmid (FIG. 1A). The mice were boosted by injecting the same amount of DNA construct three times at two week intervals in the same manner but without pre-treatment with bupivacaine-HCl.

For the recombinant gp160 immunization, BALB/C mice were initially immunized with 1 μg of glycosylated recombinant (HIV-1/III$_B$) gp160 (MicroGeneSys Inc.) in complete Freund's adjuvant followed by three boosters of 1 μg of gp160 each in incomplete Freund's adjuvant at two week intervals. The production of antibody against HIV-1 gp160 was determined by testing the mouse sera for their ability to immunoprecipitate gp160. Immunoprecipitation was performed using 1×10⁶ cpm of $^{125}$I labeled rgp160, mouse sera and protein-G agarose beads (GIBCO, Inc.) as previously described by Osther, K., et al., (1991) *Hybridoma* 10:673–683, which is incorporated herein by reference. The specific precipitations were analyzed by 10% SDS-PAGE. Lane 1 is 1 μl of preimmune mouse serum reacted with the $^{125}$I-gp160. Lane 2 is 1 μl of mouse serum immunized from the pM160 immunized mice. Lane 3 is 1 μl of 1:100 dilution of ID6 monoclonal anti-gp120 antibody (Ugen, K. E., et al., (1992) *Generation of Monoclonal Antibodies Against the Amino Region of gp120 Which Elicits Antibody Dependent Cellular Cytotoxicity*, Cold Spring Harbor Laboratory) as a positive control. The arrow indicates the specifically immunoprecipitated 125I-gp160 envelope glycoprotein.

Figure 2:
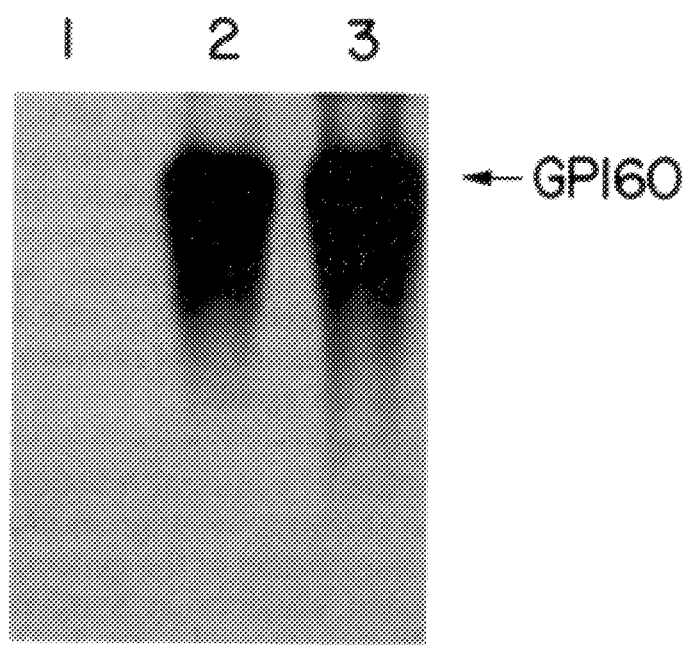
FIG. 2 is an photograph of an autoradiogram showing immunoprecipitations of serum antibodies binding to $^{125}$I-gp160.

$^{125}$I-labelled gp160 was specifically immunoprecipitated with antisera derived from the pM160-immunized animals (FIG. 2, lane 2) as well as the positive control anti-gp120 monoclonal antibody, ID6 (FIG. 2, lane 3). In contrast, the preimmune sera (FIG. 2, lane 1) only showed minimal activity in the same assay.

Eight of ten mice immunized with the pM160 construct were positive for reactivity against gp160 as determined by ELISA and the immune responses from the animal with the highest anti-gp160 titer was analyzed in detail. Four mice immunized with the control vector all showed a similar negative reactivity to gp160 in ELISA and one of these sera was used as the control for subsequent experiments.

It has been shown that HIV neutralizing antibodies are specifically targeted to several epitopes in gp120 and gp41, which include the V3 loop in gp120 (Goudsmit, J. et al., (1988) *AIDS* 2:157–164; and Putney, S. D., et al., (1989) *Development Of An HIV Subunit Vaccine*, Montreal), the CD4 binding site near the carboxy terminus of gp120 (Lasky, L. A., et al., (1987) *Cell* 50:975–985) as well as the immunodominant loop of gp41 just downstream of the N-terminal fusion region (Schrier, R. D., et al., (1988) *J. Virol.* 62:2531–2536).

Figure 3A:
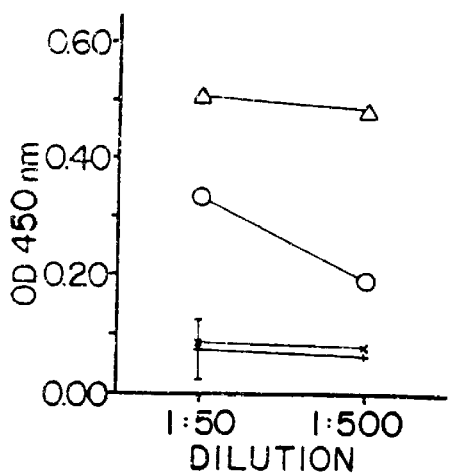
FIGS. 3A–3E are graphs showing ELISA results binding different sera to various proteins immobilized on microtiter plates.
Figure 3B:
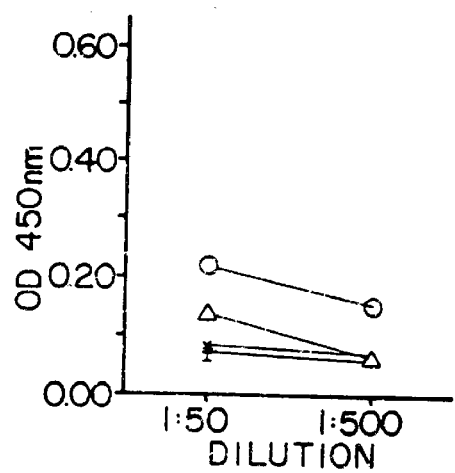
Figure 3C:
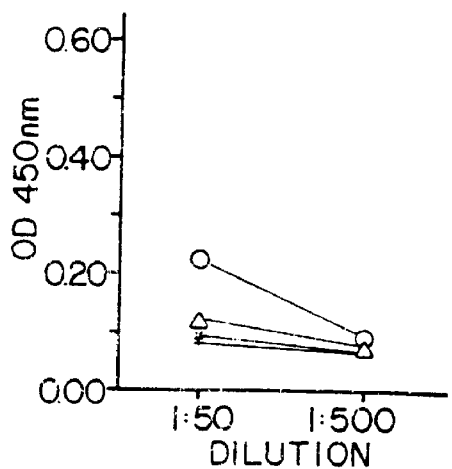
Figure 3D:
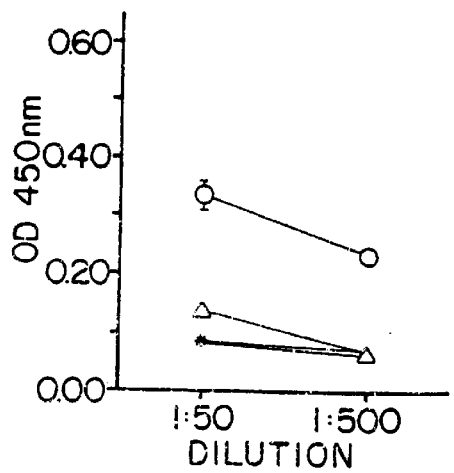
Figure 3E:
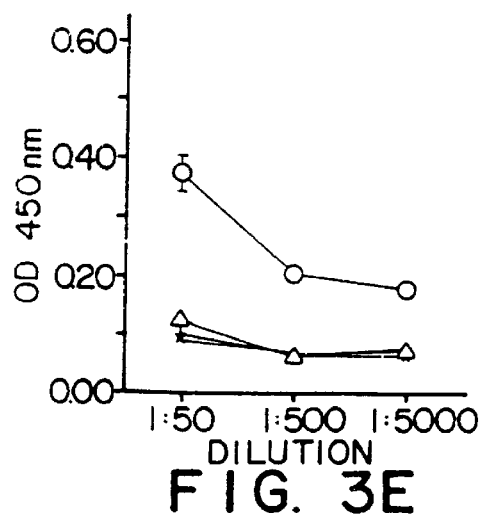

To determine whether the anti-gp160 antibodies elicited in these mice are reactive to these important regions of the envelope glycoproteins, peptides for the BRU/V3 loop, peptides for the MN/V3 loop, peptides for the HXB2/gp41 N-terminus or peptides for HXB2/CD4 binding site were absorbed to microtiter plates and specific reactivities of the mouse antisera determined in ELISA assays. One μg/ml of gp160 or 10 μg/ml of each peptide was coated to microtiter plates in 0.1M bicarbonate buffer (pH 9.5) overnight at 4° C., blocked with 2% bovine serum albumin in PBS, and reacted with goat anti-mouse IgG conjugated with HRPO (Fisher) for one hour at 37° C. and developed with TMB substrate (Sigma) for 10–30 minutes at room temperature in the dark. Results are reported in FIG. 3. Antisera were as follows: (-+-) is preimmune sera, (-x-) is the pMAMneoBlue vector immunized sera, (-O-) is the pM160 immunized sera, (-Δ-) is from mice immunized with the rgp160 protein. FIG. 3A shows results using a rgp160 protein coated plate. FIG. 3B shows results using a BRU/V3 loop peptides (CNTRKRIRIQRGPGRAFVTIGK (SEQ ID NO:13)) coated plate. FIG. 3C shows results using a plate coated with MN/V loop peptides (YNKRKRIHIQRGPGRAFYTTKNIIC (SEQ ID NO:14)) with the QR sequence from HIV-1/III$_B$ in bold-faced type. FIG. 3D shows the results using a HXB2/CD4 binding site peptides (CRIKQFINMWQEVGKAMYAPPISGIRC (SEQ ID NO:15)) coated plate. FIG. 3E shows the results using a BRU/gp41 immunodominant region peptides (RILAVERYIKDQQLLGIWGCSGKLIC (SEQ ID NO:16)) coated plate.

For the recombinant gp160 immunization. BALB/C mice were initially immunized with 1 μg of glycosylated recombinant (HIV-1/III$_B$) gp160 (MicroGeneSys Inc.) in complete Freund's adjuvant followed by three boosters of 1 μg of gp160 each in incomplete Freund's adjuvant at two week intervals.

FIG. 3 shows that antiserum from the pM160 construct immunized mouse has significantly higher reactivity to the BRU and MN/V3 loop peptides, the CD4 binding site peptide and the immunodominant gp41 peptide than the recombinant gp160 protein (rgp160 ) immunized serum. Interestingly, the antiserum from the rgp160 immunized mouse had much higher titer against the rgp160 than the pM160 immunized antiserum, but lower activity against the three specific neutralization epitopes of gp160 tested (FIG. 3 *a–d*).

To determine whether the antisera generated by DNA immunization possessed antiviral activity, the ability of the antisera to neutralize HIV-1 infection was examined. Cell-free HIV-1/III$_B$ virus at 100 TCID$_{50}$ was incubated with serial dilutions of the antisera before being used to infect MT-2 target cells (Montefiori, D. C., (1988) *J. Clin. Microbio.* 26:231–235).

One hundred TCID$_{50}$HIV-1/III$_B$ cell-free virus was preincubated with serial dilutions of antisera for one hour at 37° C. Following incubation the pretreated virus was then plated on the 4×10$^4$ of target cell line, MT-2 for one hour at 37° C., following infection the MT-2 cells were washed three times and then incubated at 37° C. at 5% CO$_2$. Fusion was evaluated three days later quantitatively by visually counting the number of syncytia per well in triplicate experiments under a phase contrast microscope.

The results are reported in FIG. 4. FIG. 4A shows the results using vector-immunized mouse sera compared with FIG. 4B which shows the results using pM160 immunized sera. Neutralization values (V$_n$/V$_o$) versus the dilution factors (Nara, P., (1989) *Techniques In HIV Research* eds. Aldovini, A. & Walkter, B. D., 77–86 M Stockton Press) are illustrated in FIG. 4C. The control serum (-x) was from pMAMneoBlue vector immunized mice. The test sera (O) were from pM160 immunized mice.

Figure 4A:
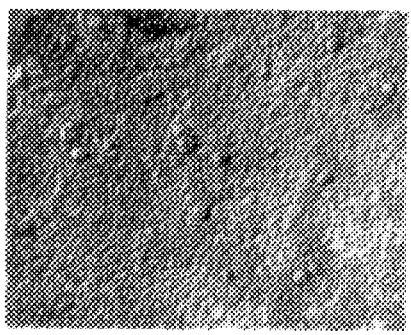
FIGS. 4A and 4B are photographs of MT-2 cells infected with $TCID_{50}$HIV-1/III$_B$ cell-free virus that was preincubated with serial dilutions of antisera.
Figure 4B:
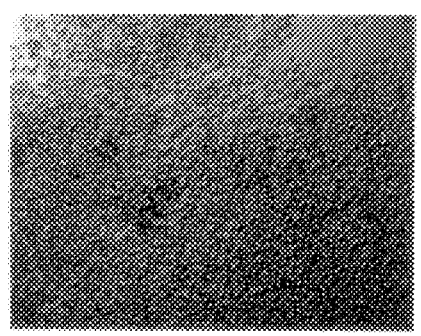
Figure 4C:
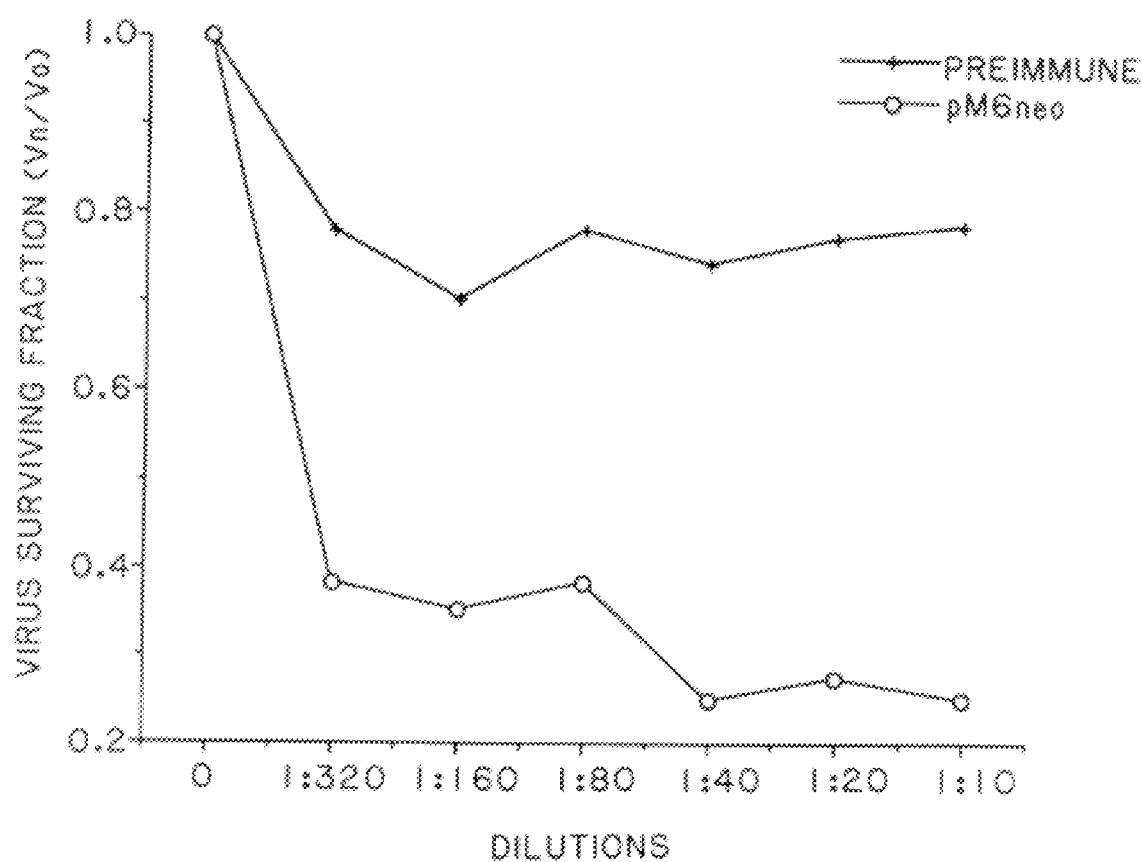
FIG. 4C is a graph illustrating the neutralization values ($V_n/V_o$) versus the dilution factors from results using control serum (x=pMAMneoBlue vector-immunized mice) and test sera (O=pM160-immunized mice).
Figure 4D:
FIGS. 4D–4G are photographs of H9/III$_B$ cells used in experiments to examine syncytial inhibition using sera from immunized and control animals.
Figure 4E:
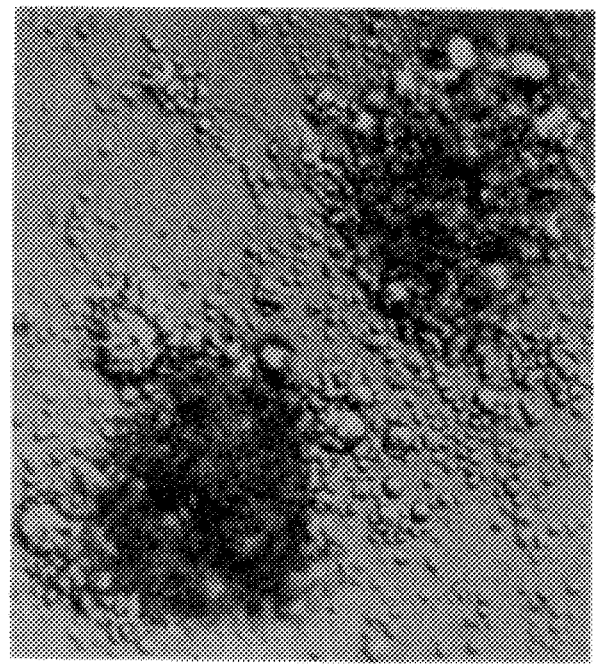
Figure 4F:
Figure 4G:
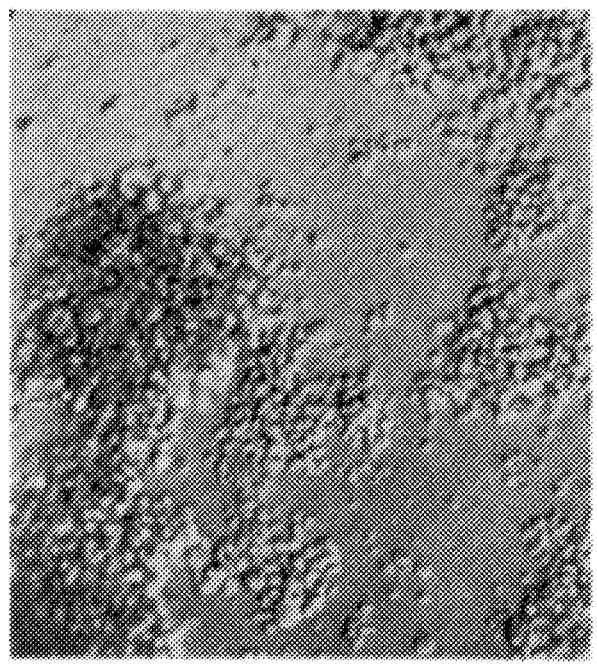
Figure 5:
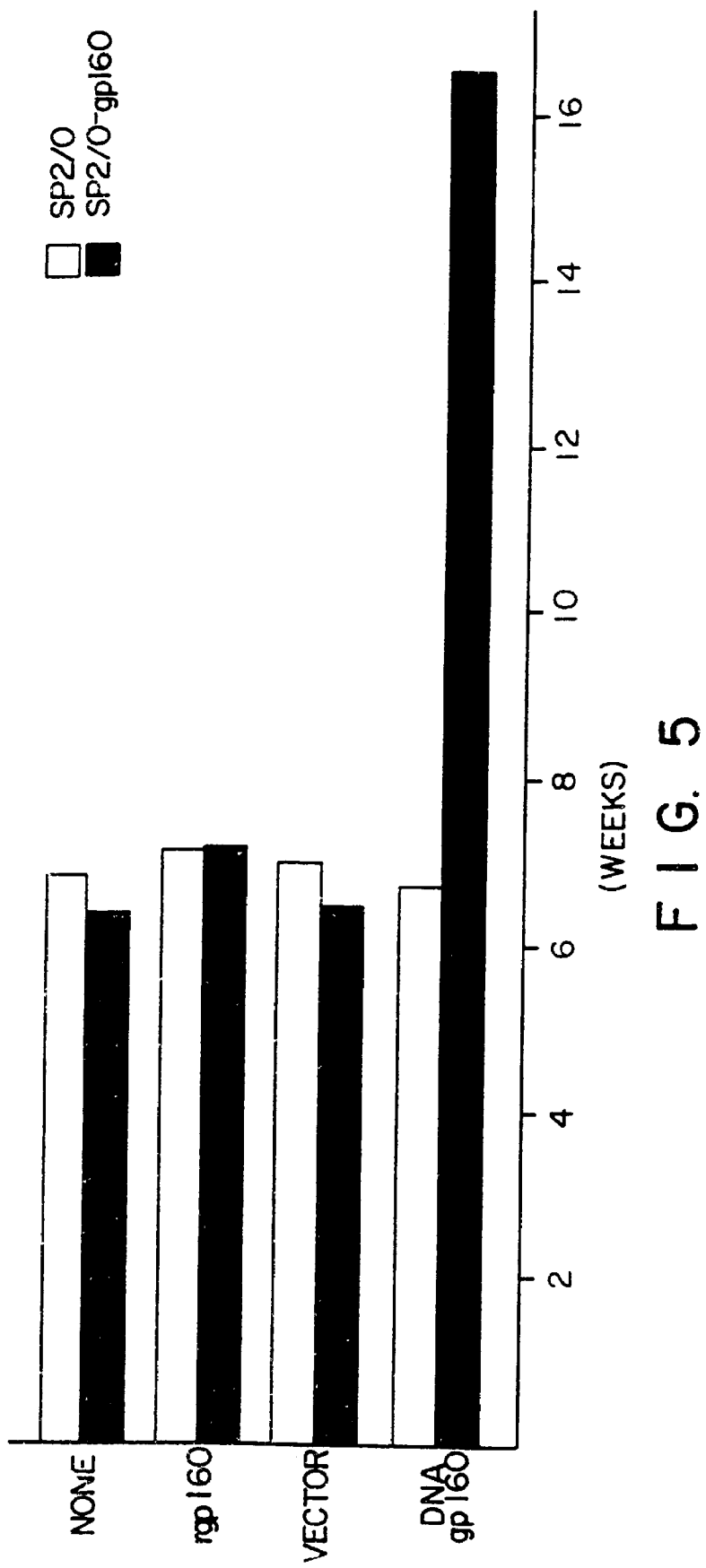
FIG. 5 is a chart depicting the survival of immunized and non-immunized mice challenged with HIV gp160-labelled and unlabelled tumor cells. Mice were immunized with recombinant gp160 protein, vector DNA only or recombinant vector comprising DNA encoding gp160. SP2/0 tumor cells or SP2/0-gp160 (SP2/0 cells transfected with DNA encoding gp160 and expressing gp160) tumor cells were introduced into the mice.
Figure 6:
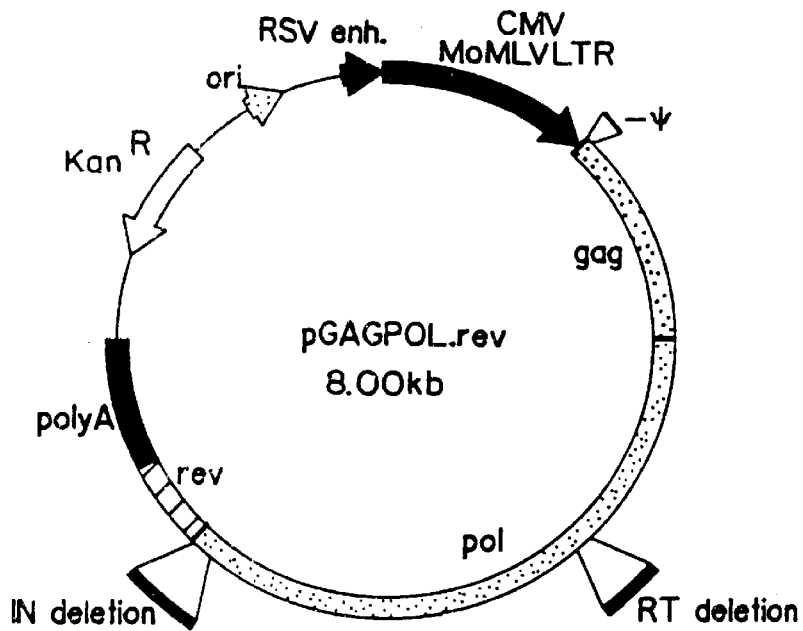
FIG. 6 is a plasmid map of pGAGPOL.rev.
Figure 7:
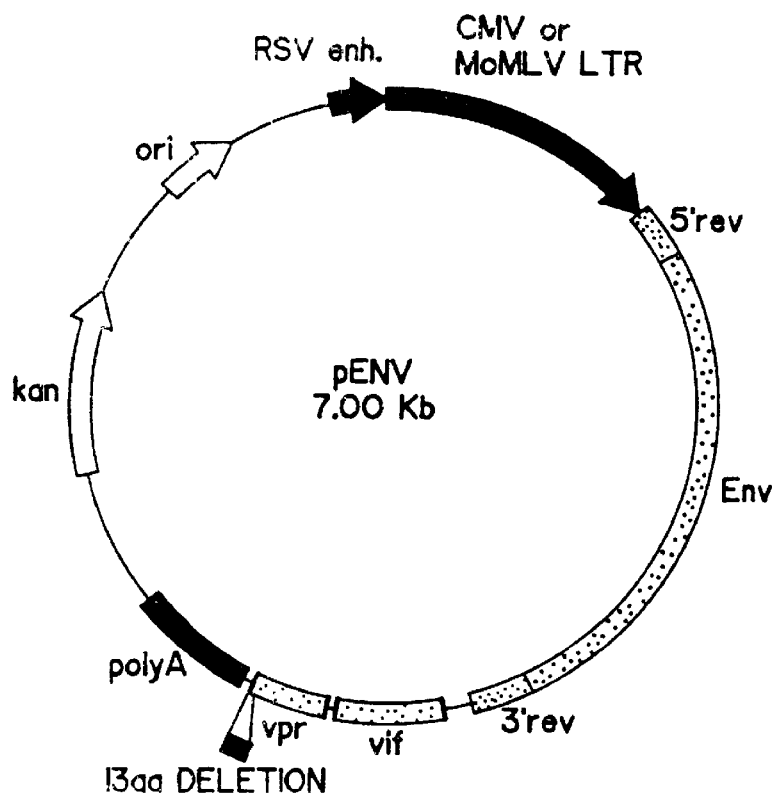
FIG. 7 is a plasmid map of pENV.

Syncytia inhibition was performed as described by Osther, K., et al., (1991) *Hybridoma* 10:673–683. The H9/III$_B$ cell line was pre-incubated with serial dilutions (1:100, 1:200, and 1:400) of antisera were made in 96 well plates in a total volume of 50 μl for thirty minutes at 37° C. at 5% CO$_2$. Fusion was evaluated three days later quantitatively by visually counting the number of syncytia per well under a phase construct microscope. FIG. 4D is the target cells co-cultivated with HIV-1/III$_B$ cell line treated with preimmune serum. FIG. 4E is the same as FIG. 4D but treated with vector control immunized serum. FIG. 4F is the same as FIG. 4D but treated with rgp160 immunized serum. FIG. 4G is the same as FIG. 4D but treated with pM160 immunized serum. FIGS. 4D to 4G show that inhibition of syncytia was apparent at dilution at 1:200 in these assays. MT-2 cells were infected with cell-free HIV-1/III$_B$ which had been preincubated with vector-immunized antiserum readily formed syncytia (FIG. 4A). In comparison, preincubation with pM160 immunized mouse serum prevented syncytium formation (FIG. 4B). The neutralization kinetics were determined by V$_n$/V$_o$ versus serial dilutions of antisera (Nara, P., (1989) *Techniques In HIV Research*, eds. Aldovini, A. & Walker, B. D., 77–86, M Stockton Press) (FIG. 4C). The serum from the pM160 immunized mouse had biologically active neutralizing activity at dilutions of up to 1:320 while control antisera did not show similar activity.

To determine if the antiserum from the pM160 immunized mouse could inhibit envelope-mediated virus spread through direct cell-to-cell fusion, syncytium inhibition assays were performed. Antiserum from the pM160 immunized mouse inhibits HIV-1 induced syncytium formation at 1:200 dilutions (FIG. 4G). In contrast, the preimmune sera (FIG. 4D), antisera from the rgp160 immunized mice (FIG. 4F) and antisera from the control vector-immunized animals (FIG. 4E) failed to inhibit syncytium formation at the same dilutions.

Observations from the neutralization (FIGS. 4A–C) and syncytium inhibition assays (FIGS. D–G) of these sera correlates with the observed ELISA reactivities (FIG. 3). The antiserum from the pM160 immunized mouse which showed a high level of binding to neutralizing epitopes likewise demonstrated high level anti-viral activities; conversely, sera with little binding to these epitopes including the antiserum from rgp160 immunized mice have low anti-viral activity.

Low level neutralizing activity has been observed by other groups when using rgp160 immunization (Lasky, L. A. et al., (1986) *Science* 233:209–212; and Berman P. W., et al., (1990) *Nature* 345:622–625. The reasons for the more effective generation of anti-viral activities by the genetic immunization than by recombinant protein immunization are not clear. However, the differences in the generated immune responses may be due to the introduction of the gp160 gene directly into the mouse muscle cells and expression of this gene in vivo which may correctly process the products and lead to more effective processing of the target antigen.

HIV enters cells binding to the CD4 molecule found predominantly on human helper T-cells, macrophages, and possibly glial cells (Maddon, P. J., et al., (1986) *Cell* 47:333–348; Koenig, S., et al., (1986) *Science* 233:1089–1093; and Cheng-Mayer, C., et al., (1987) *Proc. Natl. Acad. Sci. USA* 84:3526–3530). Interruption of this binding has been shown to prevent HIV infection in vivo (Fisher, R. A., et al., (1988) *Nature* 331:76–78; and Sun, H. C., et al., 1989 *J. Virol.* 63:3579–85).

To test whether the antisera from pM160 immunized mice can inhibit gp120 binding to CD4-bearing T-cells, a direct inhibition assay monitored by fluorocytometry was employed (Chen, Y. H., et al., (1992) *AIDS* 6:533–539. It was observed that serum from the pM160 construct-immunized mouse was able to block the binding of gp120 to CD4-bearing T-cells: a 1:15 dilution of immune serum inhibited FITC-gp120 binding to CD4$^+$SupT1 cells by 22%±2% in replicate experiments as evaluated by flow cytometry. This indicates that this region for HIV entry into target cells can also be functionally inhibited by this antiserum. These data are consistent with observed ELISA reactivity of the antiserum to the CD4 binding site peptides (FIG. 3c).

Immunoglobulin isotyping studies were performed by using a commercial murine monoclonal antibody isotyping kit (Sigma). Of the anti-gp160 specific antibodies elicited by pM160 immunization, 19% are IgG1, 51% are IgG2, 16% are IgG3, 10% are IgM and 5% are IgA. The predominance of IgG isotypes indicates that a secondary immune response has taken place, and further suggests that helper T-cells can be elicited by genetic immunization.

To determine whether immunization with the DNA construct can lead to the generation of anti-DNA antibodies in these experimental animals, pM160 and pMAMneoBlue DNAs were coated onto microtiter plates and specific binding was determined by ELISA using sera all immunized animals. No significant binding to plasmid DNA was observed. Thus, using genetic material for inoculation into muscle tissue appears unlikely to produce an anti-plasmid DNA response.

Introducing construct DNA into mouse muscle by needle injection may cause inconsistent results, as this technique does not provide a means to control DNA uptake by muscle cells. Injection of construct DNA alone (n≈4) with bupivacaine pretreated animals (n≈4) was compared. The immune responses observed in the two groups were similar, with 85% and 75% animals responding in ELISA assays respectively. Increased efficiency may be achieved by use of a direct DNA delivery system such as particle bombardment (Klein, T. M. et al., (1992) *Bio/technology* 10:286–291.

Evidence of neutralization, syncytia inhibition, inhibition of CD4-gp120 binding, and specific binding to several important regions on the gp160 demonstrate that introduction of a DNA construct encoding HIV gp160 membrane-bound glycoprotein directly into muscle cells of living animals can elicit specific humoral responses, and generate biologically relevant anti-viral antibodies.

To test whether the vaccine is capable of eliciting a protective immune response, the animal model described above was used. Tumor cells were transfected with DNA encoding p160, confirmed to express the protein and implanted into the animal. Controls included untransfected tumor lines.

Genetically immunized animals were vaccinated with plasmid pM160 . Controls included unvaccinated animals, animals vaccinated with vector DNA only and animals administered the gp160 protein.

Results demonstrate that the immune response of genetically vaccinated mice was sufficient to completely eliminate the transfected tumors while having no effect on untranslated tumors. gp160 protein vaccination led to some reduction in tumor size in transfected tumors as compared to untransfected tumors but had no effect on mortality. Unvaccinated animals showed similar mortality for both transfected and untransfected tumors.

Example 4

The following is a list of constructs which may be used in the methods of the present invention. The vector pBabe.puro, which is used as a starting material to produce many of the below listed constructs, was originally constructed and reported by Morgenstern, J. P. and H. Land, 1990 *Nucl. Acids Res.* 18(12):3587–3596, which is incorporated herein by reference. The pBabe.puro plasmid is particularly useful for expression of exogenous genes in mammalian cells. DNA sequences to be expressed are inserted at cloning sites under the control of the Moloney murine leukemia virus (Mo MuLV) long termal repeat (LTR) promoter. The plasmid contains the selectable marker for puromycin resistance.

Example 5

Plasmid pBa.Vα3 is a 7.8 kb plasmid that contains a 2.7 kb EcoRI genomic fragment encoding the T cell receptor Va3 region containing the L, V and J segments cloned into the EcoRI site of pBabe.puro. The T cell receptor-derived target protein is useful in the immunization against and treatment of T cell mediated autoimmune disease and clonotypic T cell lymphoma and leukemia.

Example 6

Plasmid pBa.gagpol-vpr is a 9.88 kb plasmid that contains the gag/pol and vif genes from HIV/MN cloned into pBabe.puro. The vpr gene is deleted. The plasmid which contains these HIV viral genes, which encode HIV target proteins, is useful in the immunization against and treatment of HIV infection and AIDS. The HIV DNA sequence is published in Reiz, M. S., 1992 *AIDS Res. Human Retro.* 8:1549, which is incorporated herein by reference. The sequence is accessible from Genbank No.: M17449, which is incorporated herein by reference.

Example 7

Plasmid pM160 is an 11.0 kb plasmid that contains the 2.3 kb PCR fragment encoding the HIV-I/3B envelope protein and rev/tat genes cloned into pMAMneoBlue. The nef region is deleted. The plasmid which contains these HIV viral genes, which encode HIV target proteins, is useful in the immunization against and treatment of HIV infection and AIDS. The DNA sequence of HIV-1/3B is published in Fisher, A., 1985 *Nature* 316:262, which is incorporated herein by reference. The sequence is accessible from Genbank No.: K03455, which is incorporated herein by reference.

Example 8

Plasmid pBa.VL is a 5.4 kb plasmid that contains PCR fragment encoding the VL region of an anti-DNA antibody cloned into pBabe.puro at the XbaI and EcoRI sites. The antibody-derived target protein is an example of a target protein useful in the immunization against and treatment of B cell mediated autoimmune disease and clonotypic B cell lymphoma and leukemia. A general method for cloning functional variable regions from antibodies can be found in Chaudhary, V. K., et al., 1990 *Proc. Natl. Acad. Sci. USA* 87:1066, which is incorporated herein by reference.

Example 9

Plasmid pOspA.B is a 6.84 kb plasmid which contains the coding regions encoding the OspA and OspB antigens of the Borrelia burgdorferi, the spirochete responsible for Lyme's disease cloned into pBabe.puro at the BamHI and SalI sites. The PCR primers used to generate the OspA and OspB fragments are 5'-GAAGGATCCATGAAAAAATATTTATTGGG-3' (SEQ ID NO:3) and 5'-ACTGTCGACTTATTTTAAAGCGTTTTTAAG-3' (SEQ ID NO: 4). See: Williams, W. V., et al. 1992 *DNA and Cell. Biol.* 11(3):207, which is incorporated herein by reference. The plasmid which contains these pathogen genes, which encode target proteins, is useful in the immunization against Lyme's disease.

Example 10

Plasmid pBa.Rb-G is a 7.10 kb plasmid which contains a PCR generated fragment encoding the rabies G protein cloned into pBabe.puro at the BamHI site. The plasmid which contains this pathogen gene, which encodes the rabies G protein, is useful in the immunization against Rabies. The DNA sequence is disclosed in Genebank No.:M32751, which is incorporated herein by reference. See also: Anilionis, A., et al., 1981 *Nature* 294:275, which is incorporated herein by reference.

Example 11

Plasmid pBa.HPV-L1 is a 6.80 kb plasmid which contains a PCR generated fragment encoding the L1 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 12

Plasmid pBa.HPV-L2 is a 6.80 kb plasmid which contains a PCR generated fragment encoding the L2 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 13

Plasmid pBa.MNp7 is a 5.24 kb plasmid which contains a PCR generated fragment encoding the p7 coding region including the HIV MN gag (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 14

Plasmid pGA733-2 is a 6.3 kb plasmid that contains the GA733-2 tumor surface antigen cloned from the colorectal carcinoma cell line SW948 into pCDM8 vector (Seed, B. and A. Aruffo, 1987 *Proc. Natl. Acad. Sci. USA* 84:3365, which is incorporated herein by reference) at BstXI site. The tumor-associated target protein is an example of a target protein useful in the immunization against and treatment of hyperproliferative disease such as cancer. The GA733-2 antigen is a useful target antigen against colon cancer. The GA733 antigen is reported in Szala, S. et al., 1990 *Proc. Natl. Acad. Sci. USA* 87:3542–3546, which is incorporated herein by reference.

Example 15

Plasmid pT4-pMV7 is a 11.15 kb plasmid that contains cDNA which encodes human CD4 receptor cloned into pMV7 vector at the EcoRI site. The CD4 target protein is useful in the immunization against and treatment of T cell lymphoma. Plasmid pT4-pMV7 is available from the AIDS Repository, Catalog No. 158.

Example 16

Plasmid pDJGA733 is a 5.1 kb plasmid that contains the GA733 tumor surface antigen cloned into pBabe.puro at the BamHI site. The tumor-associated target protein is an example of a target protein useful in the immunization against and treatment of hyperproliferative disease such as cancer. The GA733 antigen is a useful target antigen against colon cancer.

Example 17

Plasmid pBa.RAS is a 6.8 kb plasmid that contains the ras coding region that was first subcloned from pZIPneoRAS and cloned into pBabe.puro at the BamHI site. The ras target protein is an example of a cytoplasmic signalling molecule. The method of cloning ras is reported in Weinberg 1984 *Mol. Cell. Biol.* 4:1577, which is incorporated herein by reference. Ras encoding plasmid are useful for the immunization against and treatment of hyperproliferative disease such as cancer; in particular, ras related cancer such as bladder, muscle, lung, brain and bone cancer.

Example 18

Plasmid pBa.MNp55 is a 6.38 kb plasmid which contains a PCR generated fragment encoding the p55 coding region including the HIV MN gag precursor (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 19

Plasmid pBa.MNp24 is a 5.78 kb plasmid which contains a PCR generated fragment from the pMN-SF1 template encoding the p24 coding region including the whole HIV MN gag coding region cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 20

Plasmid pBa.MNp17 is a 5.5 kb plasmid which contains a PCR generated fragment encoding the p17 coding region including the HIV MN gag (core protein) sequence cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 21

Plasmid pBa.SIVenv is a 7.8 kb plasmid which contains a 2.71 PCR generated fragment amplified from a construct containing SIV 239 in pBR322 cloned into pBabe.puro at the BamHI and EcoRI sites. The primers used are 5'-GCCAGTTTTGGATCCTTAAAAAAGGCTTGG-3' (SEQ ID NO:5) and 5'-TTGTGAGGGACAGAATTCCAATCAGGG-3' (SEQ ID NO:6). The plasmid is available from the AIDS Research and Reference Reagent Program; Catalog No. 210.

Example 22

Plasmid pcTSP/ATK.env is a 8.92 kb plasmid which contains a PCR generated fragment encoding the complete HTLV envelope coding region from HTLV-1/TSP and /ATK isolates subcloned into the pcDNA1/neo vector. The primers used are 5'-CAGTGATATCCCGGGAGACTCCTC-3' (SEQ ID NO:7) and 5'-GAATAGAAGAACTCCTCTAGAATTC-3' (SEQ ID NO:8). Plasmid pcTSP/ATK.env is reported in 1988 *Proc. Natl. Acad. Sci. USA* 85:3599, which is incorporated herein by reference. The HTLV env target protein is useful in the immunization against and treatment of infection by HTLV and T cell lymphoma.

Example 23

Plasmid pBa.MNgp160 is a 7.9 kb plasmid which contains a 2.8 kb PCR generated fragment amplified from a construct containing MNenv in pSP72 and cloned into pBabe.puro at the BamHI and EcoRI sites. The primers used are 5'-GCCTTAGGCGGATCCTATGGCAGGAAG-3' (SEQ ID NO:9) and 5'-TAAGATGGGTGGCCATGGTGAATT-3' (SEQ ID NO:10). Reiz, M. S., 1992 *AIDS Res. Human Retro.* 8:1549, which is incorporated herein by reference. The sequence is accessible from Genbank No.:M17449, which is incorporated herein by reference. The plasmid which contains these HIV viral genes, which encode HIV target proteins, is useful in the immunization against and treatment of HIV infection and AIDS.

Example 24

Plasmid pC.MNp55 is a 11.8 kb plasmid which contains a 1.4 kb PCR generated fragment amplified from the gag region of MN isolate and cloned into the pCEP4 vector. The plasmid which contains these HIV viral genes, which encode HIV target proteins, is useful in the immunization against and treatment of HIV infection and AIDS. Reiz, M. S., 1992 *AIDS Res. Human Retro.* 8: 1549, which is incorporated herein by reference. The sequence is accessible from Genbank No.: M17449, which is incorporated herein by reference.

Example 25

Plasmid pC.Neu is a 14.2 kb plasmid that contains a 3.8 kb DNA fragment containing the human neu oncogene coding region that was cut out from the LTR-2/erbB-2 construct and subcloned into the pCEP4 vector. The pC.Neu plasmid is reported in DiFiore 1987 *Science* 237:178, which is incorporated herein by reference. The neu oncogene target protein is an example of a growth factor receptor useful as a target protein for the immunization against and treatment of hyperproliferative disease such as cancer; in particular, colon, breast, lung and brain cancer.

Example 26

Plasmid pC.RAS is a 11.7 kb plasmid that contains a 1.4 kb DNA fragment containing the ras oncogene coding region that was first subcloned from pZIPneoRAS and subcloned into pCEP4 at the BamHI site. The pC.RAS plasmid is reported in Weinberg 1984 *Mol. Cell. Biol.* 4:1577, which is incorporated herein by reference. The ras target protein is an example of a cytoplasmic signalling molecule. Ras encoding plasmid are useful for the immunization against and treatment of hyperproliferative disease such as cancer; in particular, ras related cancer such as bladder, muscle, lung, brain and bone cancer.

Example 27

Plasmid pNLpuro is a 15 kb plasmid which contains HIV gag/pol and SV40-puro insertion. The plasmid which contains these HIV viral genes, which encode HIV target proteins, is useful in the immunization against and treatment of HIV infection and AIDS.

Example 28

A DNA construct was designed to test the effectiveness of a genetic vaccine against human CD4 in mice. These experiments were designed to test the ability of a vaccine to protect against a T lymphoma antigen. In T cell lymphoma, CD4 is a tumor specific antigen. Accordingly, this model demonstrates the ability of the genetic vaccine to protect against T lymphoma. Further, these experiments tested the effectiveness against a member of the immunoglobulin superfamily of molecules. CD4 is highly conserved between human and murine species.

The animal model used was described above. Tumor cells were transfected with DNA encoding CD4, confirmed to express the protein and implanted into the animal. Controls included untransfected tumor lines. Although the animals were immunocompetent, an immune response was not directed against the implanted, CD4-labelled tumors in unvaccinated animals.

Genetically immunized animals were vaccinated with plasmid pT4-pMV7, a 11.15 kb plasmid that contains cDNA which encodes human CD4 receptor cloned into pMV7 vector at the EcoRI site. Plasmid pT4-pMV7 is available from the AIDS Repository, Catalog No. 158. Controls included unvaccinated animals and animals administered the CD4 protein.

In the genetic immunization procedure described herein, the quadriceps muscles of BALB/c mice were injected with 100 μl of 0.5% bupivacaine-HCl and 0.1% methylparaben in isotonic NaCl using a 27-gauge needle to stimulate muscle cell regeneration (Thomason, D .B. et al., (1990) *Cell Physiol.* 27:C578–581). Twenty-four hours later, the same injection sites were then injected with either 100 μg of pT4-pMV7 or with 100 μg of pMV7 as a control plasmid. The mice were boosted by injecting the same amount of DNA construct three times at two week intervals in the same manner but without pre-treatment with bupivacaine-HCl.

Animals received 1,000,000 CD4-labelled tumor cells. In non-vaccinated animals, large tumors formed and death resulted after about 7–10 weeks. Vaccinated animals did not develop similar deadly tumors.

Results demonstrate that the immune response of genetically vaccinated mice was sufficient to completely eliminate the transfected tumors while having no effect on untransfected tumors. CD4 protein vaccination led to some reduction in tumor size in transfected tumors as compared to untransfected tumors but had no effect on mortality. Unvaccinated animals showed similar mortality for both transfected and untransfected tumors.

Example 29

A DNA construct was designed to test the effectiveness of a genetic vaccine against human GA733 in mice. These experiments were designed to test the ability of a vaccine to protect against GA733 associated cancer such as colon cancer. The animal model used was described above. Tumor cells were transfected with DNA encoding GA733, confirmed to express the protein and implanted into the animal. Controls included untransfected tumor lines.

Genetically immunized animals were vaccinated with plasmid pGA733-2, a 6.3 kb plasmid that contains the GA733-2 tumor surface antigen cloned from the colorectal carcinoma cell line SW948 into pCDM8 vector at BstXI site following the method described above. Controls included unvaccinated animals and animals administered the GA733 protein.

Results demonstrate that the immune response of genetically vaccinated mice was sufficient to completely eliminate the transfected tumors while having no effect on untransfected tumors. GA733 protein vaccination led to some reduction in tumor size in transfected tumors as compared to untransfected tumors but had no effect on mortality. Unvaccinated animals showed similar mortality for both transfected and untransfected tumors.

Example 30

A DNA construct was designed to test the effectiveness of a genetic vaccine against human p185neu in mice. These experiments were designed to test the ability of a vaccine to protect against p185neu associated cancer such as breast, lung and brain cancer. The animal model used was described above. Tumor cells were transfected with DNA encoding neu, confirmed to express the protein and implanted into the animal. Controls included untransfected tumor lines.

Genetically immunized animals were vaccinated with plasmid pLTR-2/erbB-2, a 14.3 kb plasmid that contains the human neu oncogene coding region cloned into the LTR-2 vector at the XhoI site following the method described above. The 5'LTR and 3'LTR are from Moloney-MuLV LTR. Controls included unvaccinated animals and animals administered the p185neu protein.

Results demonstrate that the immune response of genetically vaccinated mice was sufficient to completely eliminate the transfected tumors while having no effect on untransfected tumors. p185 protein vaccination led to some reduction in tumor size in transfected tumors as compared to untransfected tumors but had no effect on mortality. Unvaccinated animals showed similar mortality for both transfected and untransfected tumors.

Example 31

A DNA construct was designed to test the effectiveness of a genetic vaccine against human Ras in mice. These experiments were designed to test the ability of a vaccine to protect against Ras associated cancer such as bladder, muscle, lung, brain and bone cancer. The animal model used was described above. Tumor cells were transfected with DNA encoding Ras, confirmed to express the protein and implanted into the animal. Controls included untransfected tumor lines.

Genetically immunized animals were vaccinated with plasmid pBa.RAS is a 6.8 kb plasmid that contains the ras coding region that was first subcloned from pZIPneoRAS and cloned into pBabe.puro at the BamHI site following the vaccination method described above. The ras target protein is an example of a cytoplasmic signalling molecule. The method of cloning ras is reported in Weinberg 1984 *Mol. Cell. Biol.* 4:1577, which is incorporated herein by reference. Controls included unvaccinated animals and animals administered the Ras protein.

Example 32

A DNA construct was designed to test the effectiveness of a genetic vaccine against human rabies G protein antigen in mice. The animal model used was described above. Tumor cells were transfected with DNA encoding rabies G protein, confirmed to express the protein and implanted into the animal. Controls included untransfected tumor lines.

Genetically immunized animals were vaccinated with plasmid pBa.Rb-G is a 7.10 kb plasmid which contains a PCR generated fragment encoding the rabies G protein cloned into pBabe.puro at the BamHI site, following the vaccination method described above. The rabies G target protein is an example of a pathogen antigen. The DNA sequence is disclosed in Genebank No.:M32751. Controls included unvaccinated animals and animals administered the G protein.

Example 33

A DNA construct was designed to test the effectiveness of a genetic vaccine against Lyme's disease antigen in mice. The animal model used was described above. Tumor cells were transfected with DNA encoding OspA and Osp B, confirmed to express the protein and implanted into the animal. Controls included untransfected tumor lines.

Genetically immunized animals were vaccinated with plasmid pOspA.B is a 6.84 kb plasmid which contains the coding regions encoding the OspA and Osp.B antigens of the Borrelia burgdorferi, the spirochete responsible for Lyme's disease cloned into pBabe.puro at the BamHI and SalI sites, following the vaccination method described above. The OspA and OspB target proteins are examples of pathogen antigens. The PCR primers used to generate the OspA and OspB fragments are 5'-GAAGGATCCATGAAAAAATATTTATTGGG-3' (SEQ ID NO:3) and 5'-ACTGTCGACTTATTTTAAAGCGTTTTAAG-3' (SEQ ID NO: 4). See: Williams, W. V., et al. 1992 *DNA and Cell. Biol.* 11(3):207, which is incorporated herein by reference. Controls included unvaccinated animals and animals administered OspA and OspB proteins.

Example 34

A DNA construct was designed to test the effectiveness of a genetic vaccine against a human T cell receptor variable region in mice. These experiments were designed to test the ability of a vaccine to protect against a T cell receptor derived protein associated with cancer such as T cell lymphoma and T cell mediated autoimmune disease. The animal model used was described above. Tumor cells were transfected with DNA encoding Ras, confirmed to express the protein and implanted into the animal. Controls included untransfected tumor lines.

Genetically immunized animals were vaccinated with plasmid pBa.Vα3 is a 7.8 kb plasmid that contains a 2.7 kb EcoRI genomic fragment encoding the T cell receptor Vα3 region containing the L, V and J segments cloned into the EcoRI site of pBabe.puro following the vaccination method described above.

Example 35

The plasmid pM160 can be used as a starting material for several plasmids useful to express one or more genes from the env portion of HIV. As described above, the DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AGGCGTCTCGAGACAGAGGAGAGCAAGAAATG-3' (SEQ ID NO:1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. The nef gene is absent. Gene specific amplification was performed using Taq DNA polymerase according to the manufacturer's instructions (Perkin-Elmer Cetus Corp.). The PCR reaction products were treated with 0.5 ug/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech Laboratories, Inc., Palo Alto, Calif.). The resulting construct was designated as pM160. The plasmid DNA was purified with CsCl gradient ultracentrifugation. The restriction enzyme map for pMAMneoBlue plasmid is available from the manufacturer and may be used by those having ordinary skill in the art to engineer, that is to change, delete and add various elements using standard molecular biology technigues and widley available starting material.

The promoter controlling gp160/rev/tat gene expression is MMTV LTR. The promoter may be deleted and replaced with Actin promoter, myosin promoter, HIV LTR promoter and CMV promoter.

The gene conferring ampicillan resistance may be deleted or otherwise inactivated. The gene conferring neomycin resistance may be placed under the control of a bacterial promoter.

The Rous sarcoma virus enhancer may be deleted from the plasmid. The RSV enhancer may be replaced with the muscle creatine enhancer.

The gp160/rev/tat genes overlap and share the same nucleotide sequences in different reading frames. The rev gene may be deleted by changing its initiation codon to a different codon. Similarly, the tat gene may be eliminated by the same means. In each plasmid except those using the HIV LTR promoter to control gp160/rev/tat, either rev, tat, or both rev and tat may be eliminated. In plasmids using the HIV LTR promoter, tat must be present.

The following Table lists pM160-modified plasmids. Each plasmid has an inactivated ampicillin gene. Each has deleted the RSV enhancer. Some have no enhancer (no); some have creatine muscle enhancer (CME). Some have the HIV rev gene (yes) while it is deleted in others (no). Some have the HIV tat gene (yes) while it is deleted in others (no).

| Construct | Promoter | enhancer | rev | tat |
| --- | --- | --- | --- | --- |
| RA-1 | Actin | no | yes | yes |
| RA-2 | Actin | no | yes | no |
| RA-3 | Actin | no | no | yes |
| RA-4 | Actin | CME | yes | yes |
| RA-5 | Actin | CME | yes | no |
| RA-6 | Actin | CME | no | yes |
| RA-7 | CMV | no | yes | yes |
| RA-8 | CMV | no | yes | no |
| RA-9 | CMV | no | no | yes |
| RA-10 | CMV | CME | yes | yes |
| RA-11 | CMV | CME | yes | no |
| RA-12 | CMV | CME | no | yes |
| RA-13 | MMTV | no | yes | yes |
| RA-14 | MMTV | no | yes | no |
| RA-15 | MMTV | no | no | yes |
| RA-16 | MMTV | CME | yes | yes |
| RA-17 | MMTV | CME | yes | no |
| RA-18 | MMTV | CME | no | yes |
| RA-19 | Myosin | no | yes | yes |
| RA-20 | Myosin | no | yes | no |
| RA-21 | Myosin | no | no | yes |
| RA-22 | Myosin | CME | yes | yes |
| RA-23 | Myosin | CME | yes | no |
| RA-24 | Myosin | CME | no | yes |
| RA-25 | HIV-1 LTR | no | yes | yes |
| RA-26 | HIV-1 LTR | no | no | yes |
| RA-27 | HIV-1 LTR | CME | yes | yes |
| RA-28 | HIV-1 LTR | CME | no | yes |

Constructions RA-29 to RA-56 are identical to RA-1 to RA-32 respectively except in each case the promoter controlling the neomycin gene is a bacterial promoter.

Example 36

The plasmid pNLpuro may be used as a starting material to produce several different plasmids which express the HIV gag/pol genes. As described above, pNLpuro was constructed for expression of gag pol. The HIV-1 genomic clone pNL43 was obtained through the NIH AIDS Research and Reference Reagent Program (ARRRP), Division of AIDS, NIAID, NIH, from Dr. Malcom Martin, and is designated Catalog No. The pNL43 clone is a construct that consists of HIV-1 proviral DNA plus 3 kb of host (i.e. human) sequence from the site of integration (5' and 3' of the HIV sequence) cloned into pUC18. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

The vpr regulatory gene is deleted from the HIV gag pol vector in order to eliminate a necessary regulatory protein from the set of genes to be introduced by vaccination. A region from just upstream of the unique PflMI site to just after the vif termination codon was amplified via PCR using primers that introduced a non-conservative amino acid change (glu→val) at amino acid 22 of vpr, a stop codon in the vpr reading frame immediately after amino acid 22, and an EcoRI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus.

In addition to vpr, other changes may be made by those having ordinary skill in the art to plasmid pNL43puro using standard molecular biology technigues and widley available starting material.

The human flanking sequences 5' and 3' of the HIV sequences can be removed by several methods. For example, using PCR, only HIV, SV40-puro, and pUC18 sequences can be amplified and reconstructed.

The psi region of HIV, which is important in the packaging of the virus, can be deleted from pNL43puro-based plasmids. In order to delete the psi region, the pNLpuro plasmid is cut with SacI and SpeI. This digestion removes the psi region as well as the 5' LTR which is upstream and portion of the gag/pol region which is downstream of psi. In order to reinsert the deleted non-psi sequences, PCR amplification is performed to regenerate those sequences. Primers are designed which regenerate the portions of the HIV seuence 5' and 3' to psi without regenrating psi. The primers reform the SacI site at the portion of the plasmid 5' of the 5' LTR. Primers go downstream from a site upstream of the SacI site to a site just 3' of the 5' end of the psi region, generating an AatI site at the 3' end. Primers starting just 5' of the psi region also generate an AatI site and, starting 3' of the SpeI site, regenerate that site. The PCR generated fragments are digested with SacI, AatI and SpeI and ligaated together with the SacI/SpeI digested pHLpuro-psi- fragment.

The HIV 5'LTR promoter can be deleted and replaced with Moloney virus promoter, MMTV LTR, Actin promoter, myosin promoter and CMV promoter.

The HIV 3'LTR polyadenylation site can be deleted and replaced with SV40 polyadenylation site.

The gene conferring ampicillin resistance may be deleted or otherwise inactivated.

The following is a list of pNLpuro-based constructions in which HIV psi and vpr regions are deleted and human flanking regions 5' and 3' of the HIV sequences are deleted.

| Construct | Promoter | poly(A) | Amp$^r$ |
|---|---|---|---|
| LA-1 | Moloney | HIV 3'LTR | yes |
| LA-2 | Moloney | SV40 | yes |
| LA-3 | Moloney | HIV 3'LTR | no |
| LA-4 | Moloney | SV40 | no |
| LA-5 | CMV | HIV 3'LTR | yes |
| LA-6 | CMV | SV40 | yes |
| LA-7 | CMV | HIV 3'LTR | no |
| LA-8 | CMV | SV40 | no |
| LA-9 | MMTV | HIV 3'LTR | yes |
| LA-10 | MMTV | SV40 | yes |
| LA-11 | MMTV | HIV 3'LTR | no |
| LA-12 | MMTV | SV40 | no |
| LA-13 | HIV 5' LTR | HIV 3'LTR | yes |
| LA-14 | HIV 5' LTR | SV40 | yes |
| LA-15 | HIV 5' LTR | HIV 3'LTR | no |
| LA-16 | HIV 5' LTR | SV40 | no |

Constructions LA-17 to LA-32 are identical to LA-1 to LA-16 respectively except in each case at least dome of the human flanking sequence remains.

Example 37

In another construction for expressing the env gene, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV env coding region is placed under the regulatory control of the CMV promoter and SV40 polyadenylation site. The HIV env coding region was obtained as a 2.3 kb PCR fragment form HIV/3B, Genebank sequence K03455. The resulting pCEP4-based plasmid, pRA-100, is maintained extrachromosomally and produces gp160 protein.

Example 38

In another construction for expressing the env gene, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV env coding region is placed under the regulatory control of the RSV promoter and SV40 polyadenylation site. The HIV env coding region was obtained as a 2.3 kb PCR fragment form HIV/3B, Genebank sequence K03455. The resulting pCEP4-based plasmid, pRA-101, is maintained extrachromosomally and produces gp160 protein.

Example 39

In another construction for expressing the gag/pol genes, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pCEP4-based plasmid, pLA-100, is maintained extrachromosomally and produces GAG55, reverse transcriptase, protease and integrase proteins.

Example 40

In another construction for expressing the gag/pol genes, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pREP4-based plasmid, pLA-101, is maintained extrachromosomally and produces GAG55, reverse transcriptase, protease and integrase proteins.

Example 41

The following construction, referred to herein as pGAGPOL.rev, is useful to express HIV gag/pol genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pGAGPOL.rev include a sequence that encodes gag; a sequence that encodes pol; a sequence that encodes reverse transcriptase which contains a small deletion; a sequence that encodes the inactive amino terminus of Int; and a sequence that encodes rev. Each of the HIV sequences are derived from HIV-1 strain HXB2.

Several safety features are included in PGAGPOL.rev. These include use of the CMV promoter and a non-retroviral poly(A) site. Furthermore, deletion of the ψ sequence limits the ability to package viral RNA. In addition, multiple mutations of the reverse transcriptase yield an enzymatically inactive product. Moreover, a large deletion of integrase yields an inactive product and a Kanamycin resistance marker is used for stabilizing bacterial transformants.

Plasmid pGAGPOL.rev is constructed as follows.

Step 1. A subclone of part of the HIV-1 (HXB2) genome that is cloned into Bluescript (Stratagene) is used. The subclone of HIV-1 contains the complete 5' LTR and the rest of the HIV-1 genome to nucleotide 5795 (Genebank numbering). The HIV-1 sequences are obtained from the HXB2D plasmid (AIDS Repository).

Step 2. PCR part of gag from the open reading frame HXB2D plasmid (AIDS Repository). Cut PCR fragment with NotI and SpeI and ligate with HIV-1 subclone described above restricted with NotI and SpeI.

Step 3. PCR gag/pol junction and part of pol-encoding sequences from the HXB2D plasmid (AIDS Repository) with primers SEQ ID NO.:17 and SEQ ID NO.:18. Cut PCR product with ClaI and ligate together. Cut ligated fragments with BclI and SalI and ligate with plasmid from Step 2 digested with BCII and SalI.

Step 4. Cut plasmid from Step 3 with BspMI and EcoRI and religate with adapters formed by annealing linkers SEQ ID NO.:19 and SEQ ID NO.:20.

Step 5. Cut plasmid from Step 4 with NotI and SalI and ligate with plasmid from either 4a or 4b in description written for pENV (below). Cut also with NotI and SalI.

Step 6. Restrict plasmid from Step 5 with SalI and MluI and ligate with PCR product obtained by PCR of rev with primers SEQ ID NO. :21 and SEQ ID NO. :22.

Step 7. Cut plasmid from Step 6 with NotI and ligate with product obtained by PCR of the rev repsonsive element in the HXB2D plasmid (AIDS Repository) with primers SEQ ID NO. :23 and SEQ ID NO.:24.

Steps 6 and 7 are optional.

Example 42

The following construction, referred to herein as pENV, is useful to express HIV env genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pENV include a sequence that encodes vpu; a sequence that encodes rev; a sequence that encodes gp160; a sequence that encodes 50% of nef; a sequence that encodes vif; and, a sequence that encodes vpr with a 13 amino acid carboxy-end deletion. The vpu, rev, gp160 and nef sequences are derived from HIV-1 strain MN. The vif and vpr sequences are derived from HIV-1 strain HXB2.

Several safety features are included in pGAGPOL.rev. These include use of the CMV promoter and a non-retroviral poly(A) site. Furthermore, tat has been deleted and a 50% deletion of nef yields an "inactive" nef product. In addition, vif and vpr are placed out of normal sequence and a partial deletion of vpr further ensures an inactive vpr product.

Plasmid pENV is constructed as follows.

Step 1. Start with pUC18 digested with HindIII and EcoRI. The resulting fragment that contains the ColE1 origin of replication and the laci gene should be ligated with the EcoRI/HindIII fragment from pMAMneoBlue that contains the our sarcoma virus enhancer. The resulting plasmid or pMAMneo-Blue from Clontech (Palo Alto, Calif.) can then be digested with HindIII and BgII. Using standard techniques, ligate with fragment containing kn gene obtained by PCR of geneblock plasmid (Pharmacia).

Step 2. If pMAMneo-Blue used as starting plasmid, digest with MluI and EcoRI, fill in the ends with Klenow fragment of Polymerase I and religate.

Step 3. Them, with either pMAMneo-Blue or pUC18-derived plasmid, digest with HindIII and ligate with the SV40 polyA site and early splicing region obtained by PCR of pCEP4 (Invitrogen, San Diego Calif.) with primers SEQ ID NO.:25 and SEQ ID NO.:26.

Step 4a. Digest with BamHI and ligate with the CMV promoter obtained by PCR of pCEP4 (Invitrogen, San Diego Calif.) with primers SEQ ID NO.:27 and SEQ ID NO.:28.

Step 4b. Digest with BamHI and ligate with the MOMLV LTR obtained by PCR with primers SEQ ID NO.:29 and SEQ ID NO.:30.

Step 5. Digest with NotI and MluI and ligate with GP160 coding region obtained by PCR of pMN-ST1 with primers SEQ ID NO.:31 and SEQ ID NO.:32.

Step 6. Digest with MluI and ligate with sequences that encode vif in its entirety and vpr with a 13aa carboxy-end deletion by CPR of HXB2D plasmid (AIDS Repository) with primers SEQ ID NO.:33 and SEQ ID NO.:34.

Example 43

An immunization system is provided which comprises:

a pharmaceutical composition comprising about 100 μg of pGAGPOL. rev in an isotonic, pharmaceutically acceptable solution; and, a pharmaceutical preparation comprising 100 μg of pENV in an isotonic, pharmaceutically acceptable solution. In addition, the immunization system preferably comprises a pharmaceutical composition comprising about 1 ml of 0.5% bupivacaine-HC1 and 0.1% methylparaben in an isotonic pharmaceutical carrier.

In such a preferred immunization system, a first set of administrations is performed in which bupivacaine and one of the two pharmaceutical compositions are administered intramuscularly to an individual, preferably into a muscle of an arm or buttock. Bupivacaine and the other of the two pharmaceutical compositions are administered intramuscularly to the individual at a different site, preferably remote from the site of the administration of the one pharmaceutical composition, preferably into a muscle of the other arm or buttock. Subsequence sets of administrations may be performed later in time, preferably 48 hours to two weeks or more later.

The immunization system may be used to vaccinate an individual in order to protect that individual from HIV infection or to treat an HIV infected individual with an immunotherapeutic.

TABLE 1

Picornavirus Family

| Genera: | Rhinoviruses: (Medical) responsible for ~50% cases of the common cold. |

TABLE 1-continued

| | |
|---|---|
| | Ehteroviruses: (Medical) includes polioviruses, coxsackieviruses, echoviruses, and human enteroviruses such as hepatitis A virus. |
| | Apthoviruses: (Veterinary.) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Senilis viruses, RossRiver virus and Eastern & Western E quint encephalitis. |
| | Reovirus: (Medical) Rubella virus. |
| Flariviridue Family | |
| | Examples include: (Medical) dengue, yellow fever, Japanese encephalitis, St. Louis encephalitis and tick borne encephalitis viruses. |
| Hepatitis Cuirus: (Medical) these viruses are not placed in a family yet but are believed to be either a togavirus or a flavivirus. Most similarity is with togavirus family. | |
| Coronavirus Family: | (Medical and Veterinary) Infectious bronchitis virus (poultry) Porcine transmissible gastroenteric virus (pig) Porcine hemagglutinatiny encephalomyelitis virus (pig) Feline infectious peritonitis virus (cats) Feline enteric coronavirus (cat) Canine coronavirus (dog) The human respiratory coronaviruses cause ~40 cases of common cold. EX. 224E, 0C43 Note - coronaviruses may cause non-A, B or C hepatitis Target antigens: E1 - also called M or matrix protein E2 - also called S or Spike protein E3 - also called HE or hemagglutin-elterose glycoprotein (not present in all coronaviruses) N - nucleocapsid |
| Rhabdovirus Family | |
| Genera: | Vesiliovirus |
| | Lyssavirus: (medical and veterinary) |
| rabies | |
| | Target antigen:G protein N protein |
| Filoviridue Family: (Medical) | |
| | Hemorrhagic fever viruses such as Marburg and Ebola virus |
| Paramyxovirus Family: | |
| Genera: | Paramyxovirus: (Medical and Veterinary) Mumps virus, New Castle disease virus (important pathogen in chickens) Morbillivirus: (Medical and Veterinary) Measles, canine distemper Pneuminvirus: (Medical and Veterinary) Respiratory syncytial virus |
| Orthomyxovirus Family (Medical) | |
| | The Influenza virus |
| Bungavirus Family | |
| Genera: | Bungavirus: (Medical) California encephalitis, LA Crosse Phlebovirus: (Medical) Rift Valley Fever Hantavirus: Puremala is a hemahagin fever |

TABLE 1-continued

| | |
|---|---|
| | virus |
| | Nairvirus (Veterinary) Nairobi sheep disease |
| | Also many unassigned bungaviruses |
| Arenavirus Family (Medical) | |
| | LCM, Lassa fever virus |
| Reovirus Family | |
| Genera: | Reovirus: a possible human pathogen |
| | Rotavirus: acute gastroenteritis in children |
| | Orbiviruses: (Medical and Veterinary) |
| | Colorado Tick fever, Lebombo (humans) equine encephalosis, blue tongue |
| Retrovirus Family | |
| Sub-Family: | |
| | Oncorivirinal: (Veterinary) (Medical) |
| | feline leukeinia virus, HTLVI and HTLVII |
| | Lentivirinal: (Medical and Veterinary) |
| | HIV, feline immunodeficiency virus, |
| | equine infections, anemia virus |
| | Spumavirinal |
| Papovavirus Family | |
| Sub-Family: | Polyomaviruses: (Medical) BKU and JCU |
| viruses | |
| Sub-Family: | Papillomavirus: (Medical) many viral types associated with cancers or malignant progression of papilloma |
| Adenovirus (Medical) | |
| | EX AD7, ARD., O.B. - cause respiratory disease - some adenoviruses such as 275 causes enteritis |
| Parvovirus Family (Veterinary) | |
| | Feline parvovirus: causes feline enteritis |
| | Feline panleucopeniavirus |
| | Canine parvovirus |
| | Porcine parvovirus |
| Herpesvirus Family | |
| Sub-Family: | alphaherpesviridue |
| Genera: | Simplexvirus (Medical) |
| | HSVI, HSVII |
| | Varicellovirus: (Medical - Veterinary) |
| | pseudorabies - varicella zoster |
| Sub-Family - | betaherpesviridue |
| Genera: | Cytomegalovirus (Medical) |
| | HCMV |
| | Muroinega lovirus |
| Sub-Family: | Gammaherpesviridue |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Variola (Siuallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Enteiuopoxviridue |
| Hepadnavirus Family | |
| | Hepatitis B virus |
| Unclassified | |
| | Hepatitis delta virus |

TABLE 2

Bacterial pathogens

Pathogenic gram-positive cocci include: pneumococcal; staphylococcal; and streptococcal. Pathogenic gram-negative cocci include: meningococcal; and gonococcal. Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum listeria monocytogenes; erysipelothrix rhusiopathiae; diphtheria; cholera; anthrax; donovanosis (granuloma inguinale); and bartonellosis. Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infeations include rickettsial and riakettsioses.
Examples of mycoplasma and chlamydial infections include: mycoplasma pneumoniae; lymphogranuloma venereum; psittacosis; and perinatal chlamydial infections Pathogenic eukaryotes Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

We claim:

1. A method of immunizing an individual against a pathogen comprising the steps of:

injecting into skeletal muscle tissue of said individual at a site on said individual's body, bupivacaine and a DNA molecule that comprises a DNA sequence that encodes an antigen from said pathogen, said DNA sequence operatively linked to regulatory sequences which control the expression of said DNA sequence;

wherein said DNA molecule is taken up by cells in said skeletal muscle tissue, said DNA sequence is expressed in said cells and a protective immune response is generated against said antigen.

2. The method of claim 1 wherein said pathogen is an intracellular pathogen.

3. The method of claim 1 wherein said pathogen is a virus.

4. The method of claim 1 wherein said pathogen is a virus selected from the group consisting of: human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus.

5. The method of claim 1 wherein said pathogen is Herpes simplex 2 virus, HSV2.

6. The method of claim 1 wherein said pathogen is Hepatitis B virus, HBV.

7. The method of claim 1 wherein said pathogen is human T cell leukemia virus, HTLV.

8. A method of treating an individual who has a hyperproliferative disease comprising:

injecting into skeletal muscle tissue of said individual at a site on said individual's body, bupivacaine and a DNA molecule that comprises a DNA sequence that encodes a hyperproliferative disease-associated protein operatively linked to regulatory sequences;

wherein said DNA molecule is taken up by cells in said skeletal muscle tissue, said DNA sequence is expressed in said cells, and a therapeutically effective immune response is generated against said hyperproliferative disease-associated protein, said immune response being directed at hyperproliferating cells expressing said hyperproliferative disease-associated protein.

9. The method of claim 8 wherein said hyperproliferative disease is cancer.

10. The method of claim 8 wherein said hyperproliferative disease is a lymphoma.

11. The method of claim 8 wherein said hyperproliferative disease is T cell lymphoma and said hyperproliferative disease-associated protein is a T cell antigen.

12. The method of claim 8 wherein said hyperproliferative disease is T cell lymphoma and said DNA sequence encodes a variable region of a T cell receptor.

13. The method of claim 8 wherein said hyperproliferative disease is a melanoma.

14. A method of treating an individual who is infected by a pathogen comprising:

injecting into skeletal muscle tissue of said individual at a site on said individual's body, bupivacaine and a DNA molecule that comprises a DNA sequence that encodes an antigen from said pathogen, said DNA sequence operatively linked to regulatory sequences which control the expression of said DNA sequence;

wherein said DNA molecule is taken up by cells in said skeletal muscle tissue, said DNA sequence is expressed in said cells and a therapeutically effective immune response is generated.

15. The method of claim 14 wherein said pathogen is an intracellular pathogen.

16. The method of claim 14 wherein said pathogen is a virus.

17. The method of claim 14 wherein said pathogen is human immunodeficiency virus HIV.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AGGCGTCTCG AGACAGAGGA GAGCAAGAAA TG        32

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTTCCCTCTA GATAAGCCAT CCAATCACAC 30

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GAAGGATCCA TGAAAAAATA TTTATTGGG 29

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ACTGTCGACT TATTTTAAAG CGTTTTTAAG 30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GCCAGTTTTG GATCCTTAAA AAAGGCTTGG 30

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTGTGAGGGA CAGAATTCCA ATCAGGG 27

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CAGTGATATC CCGGGAGACT CCTC 24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GAATAGAAGA ACTCCTCTAG AATTC         25

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GCCTTAGGCG GATCCTATGG CAGGAAG         27

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TAAGATGGGT GGCCATGGTG AATT         24

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

AGGCGTCTCG AGACAGAGGA GAGCAAGAAA TG         32

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TTTCCCTCTA GATAAGCCAT CCAATCACAC         30

( 2 ) INFORMATION FOR SEQ ID NO:13:

( i ) SEQUENCE CHARACTERISTICS:
        ( A ) LENGTH: 22 amino acids (B) TYPE: amino acid
(D) TOPOLOGY: linear (i i) MOLECULE TYPE: peptide (x i) SEQUENCE DESCRIPTION: SEQ ID NO:13:

Cys Asn Thr Arg Lys Arg Ile Arg Ile Gln Arg Gly Pro Gly Arg Ala
1               5                   10                  15
Phe Val Thr Ile Gly Lys
                20

(2) INFORMATION FOR SEQ ID NO:14:

(i) SEQUENCE CHARACTERISTICS:
 (A) LENGTH: 25 amino acids
 (B) TYPE: amino acid
 (D) TOPOLOGY: linear (i i) MOLECULE TYPE: peptide (x i) SEQUENCE DESCRIPTION: SEQ ID NO:14:

Tyr Asn Lys Arg Lys Arg Ile His Ile Gln Arg Gly Pro Gly Arg Ala
1               5                   10                  15
Phe Tyr Thr Thr Lys Asn Ile Ile Cys
                20                  25

(2) INFORMATION FOR SEQ ID NO:15:

(i) SEQUENCE CHARACTERISTICS:
 (A) LENGTH: 27 amino acids
 (B) TYPE: amino acid
 (D) TOPOLOGY: linear (i i) MOLECULE TYPE: peptide (x i) SEQUENCE DESCRIPTION: SEQ ID NO:15:

Cys Arg Ile Lys Gln Phe Ile Asn Met Trp Gln Glu Val Gly Lys Ala
1               5                   10                  15
Met Thr Ala Pro Pro Ile Ser Gly Ile Arg Cys
                20                  25

(2) INFORMATION FOR SEQ ID NO:16:

(i) SEQUENCE CHARACTERISTICS:
 (A) LENGTH: 26 amino acids
 (B) TYPE: amino acid
 (D) TOPOLOGY: linear (i i) MOLECULE TYPE: peptide (x i) SEQUENCE DESCRIPTION: SEQ ID NO:16:

Arg Ile Leu Ala Val Glu Arg Tyr Ile Lys Asp Gln Gln Leu Leu Gly
1               5                   10                  15
Ile Trp Gly Cys Ser Gly Lys Leu Ile Cys
                20                  25

(2) INFORMATION FOR SEQ ID NO:17:

(i) SEQUENCE CHARACTERISTICS:
 (A) LENGTH: 27 base pairs
 (B) TYPE: nucleic acid
 (C) STRANDEDNESS: single
 (D) TOPOLOGY: linear (i i) MOLECULE TYPE: DNA (x i) SEQUENCE DESCRIPTION: SEQ ID NO:17:

TTGTTTAACT TTTGATCGAT CCATTCC        27

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GATTTGTATC GATGATCTGA C        21

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

TGTAGTAGCA AAAGAAATAG TTAAG        25

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

AATTCTTAAC TATTTCTTTT GCTAC        25

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

ATTTGTCGAC TGGTTTCAGC CTGCCATGGC AGGAAGAAGC        40

( 2 ) INFORMATION FOR SEQ ID NO:22:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

ACGACGCGTA TTCTTTAGCT CCTGACTCC        29

( 2 ) INFORMATION FOR SEQ ID NO:23:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:23:

GCTGACGGTA GCGGCCGCAC AATT    24

( 2 ) INFORMATION FOR SEQ ID NO:24:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:24:

GTATTAAGCG GCCGCAATTG TT    22

( 2 ) INFORMATION FOR SEQ ID NO:25:

( i ) SEQUENCE CHARACTERISTICS:
    ( A ) LENGTH: 78 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:25:

AAAAAGCTTC GCGGATCCGC GTTGCGGCCG CAACCGGTCA CCGGCGACGC GTCGGTCGAC    60

CGGTCATGGC TGGGCCCC    78

( 2 ) INFORMATION FOR SEQ ID NO:26:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:26:

CCCAAGCTTA GACATGATAA GATACATTG    29

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:27:

CTAGCAGCTG GATCCCAGCT TC    22

( 2 ) INFORMATION FOR SEQ ID NO:28:

( i ) SEQUENCE CHARACTERISTICS:
    ( A ) LENGTH: 24 base pairs
    ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:28:

GGATTTCTGG GGATCCAAGC TAGT 24

( 2 ) INFORMATION FOR SEQ ID NO:29:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:29:

TATAGGATCC GCGCAATGAA AGACCCCACC T 31

( 2 ) INFORMATION FOR SEQ ID NO:30:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:30:

ATATGGATCC GCAATGAAAG ACCCCGCTG A 31

( 2 ) INFORMATION FOR SEQ ID NO:31:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:31:

TAAAGCGGCC GCTCCTATGG CAGGAAGACG 30

( 2 ) INFORMATION FOR SEQ ID NO:32:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:32:

ATTACGCGTC TTATGCTTCT AGCCAGGCAC AATG 34

( 2 ) INFORMATION FOR SEQ ID NO:33:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA -continued (xi) SEQUENCE DESCRIPTION: SEQ ID NO:33:

ATTACGCGTT TATTACAGAA TGGAAAACAG ATGGCAGGTG    40

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

ATTACGCGTT ATTGCAGAAT TCTTATTATG GC    32